(12) United States Patent
Murray et al.

(10) Patent No.: US 11,484,578 B2
(45) Date of Patent: Nov. 1, 2022

(54) BIOMATERIAL FOR ARTICULAR CARTILAGE MAINTENANCE AND TREATMENT OF ARTHRITIS

(71) Applicants: Children's Medical Center Corporation, Boston, MA (US); Rhode Island Hospital, Providence, RI (US)

(72) Inventors: Martha M. Murray, Sherborn, MA (US); Braden C. Fleming, East Greenwich, RI (US)

(73) Assignees: Children's Medical Center Corporation, Boston, MA (US); Rhode Island Hospital, Providence, RI (US)

( * ) Notice: Subject to any disclaimer, the term of this patent is extended or adjusted under 35 U.S.C. 154(b) by 0 days.

(21) Appl. No.: 14/376,212

(22) PCT Filed: Feb. 1, 2013

(86) PCT No.: PCT/US2013/024467
§ 371 (c)(1),
(2) Date: Aug. 1, 2014

(87) PCT Pub. No.: WO2004/078134
PCT Pub. Date: Sep. 16, 2004

(65) Prior Publication Data
US 2014/0369984 A1   Dec. 18, 2014

Related U.S. Application Data

(60) Provisional application No. 61/593,415, filed on Feb. 1, 2012.

(51) Int. Cl.
| | |
|---|---|
| A61K 38/39 | (2006.01) |
| A61K 35/14 | (2015.01) |
| A61L 27/24 | (2006.01) |
| A61L 27/36 | (2006.01) |
| A61L 27/38 | (2006.01) |
| A61K 35/15 | (2015.01) |
| A61L 27/54 | (2006.01) |
| A61L 27/56 | (2006.01) |
| A61K 38/18 | (2006.01) |
| A61K 35/19 | (2015.01) |
| A61K 35/12 | (2015.01) |

(52) U.S. Cl.
CPC ............. *A61K 38/39* (2013.01); *A61K 35/15* (2013.01); *A61K 35/19* (2013.01); *A61K 38/18* (2013.01); *A61L 27/24* (2013.01); *A61L 27/3633* (2013.01); *A61L 27/3691* (2013.01); *A61L 27/3804* (2013.01); *A61L 27/3834* (2013.01); *A61L 27/54* (2013.01); *A61L 27/56* (2013.01); *A61K 2035/124* (2013.01); *A61L 2300/414* (2013.01); *A61L 2400/06* (2013.01); *A61L 2430/24* (2013.01)

(58) Field of Classification Search
CPC ................................ A61K 38/39; A61K 35/18
See application file for complete search history.

(56) References Cited

U.S. PATENT DOCUMENTS

| | | |
|---|---|---|
| 2,127,903 A | 8/1938 | Bowen |
| 3,176,316 A | 4/1965 | Bodell |
| 3,373,906 A | 3/1968 | De Hart et al. |
| 3,587,982 A | 6/1971 | Campbell |
| 3,738,535 A | 6/1973 | Nicholls |
| 3,774,604 A | 11/1973 | Danielsson |
| 3,797,499 A | 3/1974 | Schneider |
| 4,069,814 A | 1/1978 | Clemens |
| 4,186,448 A | 2/1980 | Brekke |
| 4,265,618 A | 5/1981 | Herskovitz |
| 4,458,678 A | 7/1984 | Yannas et al. |
| 4,467,806 A | 8/1984 | Bhiwandiwala et al. |
| 4,578,067 A | 3/1986 | Cruz |
| 4,585,458 A | 4/1986 | Kurland |
| 4,753,536 A | 6/1988 | Spehar et al. |
| 4,808,184 A | 2/1989 | Tepic |
| 4,808,570 A | 2/1989 | Michaeli |
| 4,834,734 A * | 5/1989 | Morganti ............. A61K 8/0208 604/304 |
| 4,846,835 A | 7/1989 | Grande |
| 4,851,513 A | 7/1989 | Devore et al. |
| 4,894,063 A | 1/1990 | Nashef |
| 4,932,942 A | 6/1990 | Maslanka |
| 4,955,893 A | 9/1990 | Yannas et al. |
| 4,959,058 A | 9/1990 | Michelson |

(Continued)

FOREIGN PATENT DOCUMENTS

| | | |
|---|---|---|
| CN | 102488713 A | 6/2012 |
| EP | 0295721 A2 | 12/1988 |

(Continued)

OTHER PUBLICATIONS

Crapo et al., "An overview of tissue and whole organ decellularization processes", Biomaterials, 2011, 32(12), pp. 3233-3243.*
Kon et al., "Platelet-rich plasma: intra-articular knee injections produced favorable results on degenerative cartilage lesions", Knee Surg Sports Traumatol Arthrosc (2010) 18:472-479. (Year: 2010).*
W.A. Macrae, Chronic pain after surgery, British Journal of Anaesthesia, 2001, vol. 87, No. 1, pp. 88-98. (Year: 2001).*
International Search Report and Written Opinion for PCT/US2013/024467 dated Apr. 29, 2013.
International Preliminary Report on Patentability for PCT/US2013/024467 dated Aug. 14, 2014.
Al-Munajjed et al., Development of a collagen calcium-phosphate scaffold as a novel bone graft substitute. Stud Health Technol Inform. 2008;133:11-20.

(Continued)

*Primary Examiner* — Laura Schuberg
(74) *Attorney, Agent, or Firm* — Fish & Richardson P.C.

(57) ABSTRACT

The present disclosure provides biomaterials and methods for preventing and minimizing progression of cartilage and/or connective tissue damage. Also provided herein are biomaterials and methods for alleviating and/or reducing the risk for developing arthritis (e.g., osteoarthritis) associated with joint injury and/or joint surgery.

13 Claims, 18 Drawing Sheets

(56) References Cited

U.S. PATENT DOCUMENTS

| | | | |
|---|---|---|---|
| 4,973,321 A | 11/1990 | Michelson | |
| 5,007,934 A | 4/1991 | Stone | |
| 5,037,396 A | 8/1991 | Streeter | |
| 5,078,744 A | 1/1992 | Chvapil | |
| 5,119,669 A | 6/1992 | Silvis et al. | |
| 5,152,462 A | 10/1992 | Evans | |
| 5,171,273 A | 12/1992 | Silver et al. | |
| 5,206,023 A | 4/1993 | Hunziker | |
| 5,275,826 A | 1/1994 | Badylak et al. | |
| 5,281,422 A | 1/1994 | Badylak et al. | |
| 5,380,087 A | 1/1995 | Haber et al. | |
| 5,436,135 A | 7/1995 | Tayot et al. | |
| 5,455,833 A | 10/1995 | Herre et al. | |
| 5,492,135 A * | 2/1996 | DeVore | A61F 9/00819 128/898 |
| 5,503,616 A | 4/1996 | Jones | |
| 5,522,840 A | 6/1996 | Krajicek | |
| 5,556,429 A | 9/1996 | Felt | |
| 5,595,621 A | 1/1997 | Light et al. | |
| 5,652,077 A | 7/1997 | Obinata | |
| 5,655,546 A | 8/1997 | Halpern | |
| 5,681,353 A | 10/1997 | Li et al. | |
| 5,749,895 A | 5/1998 | Sawyer et al. | |
| 5,810,884 A | 9/1998 | Kim | |
| 5,897,591 A | 4/1999 | Kobayashi | |
| 5,902,741 A | 5/1999 | Purchio et al. | |
| RE36,370 E | 11/1999 | Li | |
| 5,993,844 A * | 11/1999 | Abraham | A61K 35/12 424/423 |
| 6,045,569 A | 4/2000 | Kensey et al. | |
| 6,080,192 A | 6/2000 | Demopulos et al. | |
| 6,087,113 A | 7/2000 | Caplan et al. | |
| 6,096,309 A | 8/2000 | Prior et al. | |
| 6,117,425 A | 9/2000 | MacPhee et al. | |
| 6,129,757 A | 10/2000 | Weadock | |
| 6,139,520 A | 10/2000 | McCrory et al. | |
| 6,153,292 A | 11/2000 | Bell et al. | |
| 6,171,610 B1 | 1/2001 | Vacant et al. | |
| 6,176,880 B1 | 1/2001 | Plouhar et al. | |
| 6,214,049 B1 | 4/2001 | Gayer et al. | |
| 6,234,795 B1 | 5/2001 | Fischer | |
| 6,283,996 B1 | 9/2001 | Chervitz et al. | |
| 6,309,372 B1 | 10/2001 | Fischer et al. | |
| 6,322,785 B1 | 11/2001 | Gainey et al. | |
| 6,365,149 B2 | 4/2002 | Vyakarnam et al. | |
| 6,454,129 B1 | 9/2002 | Green | |
| 6,472,210 B1 | 10/2002 | Holy et al. | |
| 6,629,997 B2 | 10/2003 | Mansmann et al. | |
| 6,699,214 B2 | 3/2004 | Gellman | |
| 6,835,377 B2 | 12/2004 | Goldberg et al. | |
| 6,946,003 B1 | 9/2005 | Wolowacz et al. | |
| 6,964,685 B2 | 11/2005 | Murray et al. | |
| 6,971,787 B2 | 12/2005 | Botrie et al. | |
| 7,119,062 B1 * | 10/2006 | Alvis | A61K 9/0024 514/17.2 |
| 7,148,209 B2 | 12/2006 | Hoemann et al. | |
| 7,156,880 B2 | 1/2007 | Evans et al. | |
| 7,250,057 B2 | 7/2007 | Forsberg | |
| 7,335,220 B2 | 2/2008 | Khosravi et al. | |
| 7,652,077 B2 | 1/2010 | Cook et al. | |
| 7,838,630 B2 | 11/2010 | Murray et al. | |
| 7,901,461 B2 | 3/2011 | Harmon et al. | |
| 8,137,686 B2 | 3/2012 | Kladakis et al. | |
| 8,308,681 B2 | 11/2012 | Slocum et al. | |
| 8,642,735 B2 | 2/2014 | Murray et al. | |
| 9,308,242 B2 | 4/2016 | Murray | |
| 9,757,495 B2 | 9/2017 | Murray | |
| 9,849,213 B2 | 12/2017 | Murray | |
| 2002/0022884 A1 | 2/2002 | Mansmann | |
| 2002/0025921 A1 * | 2/2002 | Petito | A61K 38/39 514/25 |
| 2002/0061842 A1 * | 5/2002 | Mansour | A61L 2/0017 514/2.3 |
| 2002/0123805 A1 | 9/2002 | Murray et al. | |
| 2002/0161450 A1 | 10/2002 | Doi et al. | |
| 2002/0183845 A1 | 12/2002 | Mansmann et al. | |
| 2003/0012805 A1 | 1/2003 | Chen et al. | |
| 2003/0078659 A1 | 4/2003 | Yang | |
| 2003/0147935 A1 | 8/2003 | Binette et al. | |
| 2003/0163144 A1 | 8/2003 | Weadock et al. | |
| 2003/0167053 A1 | 9/2003 | Taufig | |
| 2004/0059416 A1 | 3/2004 | Murray et al. | |
| 2004/0078077 A1 | 4/2004 | Binette et al. | |
| 2004/0170664 A1 | 9/2004 | Spector et al. | |
| 2004/0258729 A1 | 12/2004 | Czernuszka et al. | |
| 2004/0262332 A1 | 12/2004 | Pauser et al. | |
| 2004/0267362 A1 | 12/2004 | Hwang et al. | |
| 2005/0027307 A1 | 2/2005 | Schwartz et al. | |
| 2005/0129730 A1 | 6/2005 | Pang et al. | |
| 2005/0183731 A1 | 8/2005 | Hunter et al. | |
| 2005/0230422 A1 | 10/2005 | Muller et al. | |
| 2005/0261736 A1 | 11/2005 | Murray et al. | |
| 2006/0018946 A1 * | 1/2006 | Prescott | A61K 38/39 424/423 |
| 2006/0251631 A1 * | 11/2006 | Adkisson | A61K 9/0019 424/93.21 |
| 2007/0269476 A1 | 11/2007 | Voytik-Harbin et al. | |
| 2009/0143765 A1 | 6/2009 | Slocum et al. | |
| 2009/0254104 A1 | 10/2009 | Murray | |
| 2009/0306776 A1 | 12/2009 | Murray | |
| 2010/0049322 A1 * | 2/2010 | McKay | A61F 2/30756 623/16.11 |
| 2010/0166862 A1 * | 7/2010 | Francois | A61K 38/12 424/484 |
| 2010/0221835 A1 | 9/2010 | Tanaka et al. | |
| 2011/0027338 A1 | 2/2011 | Murray et al. | |
| 2011/0306555 A1 | 12/2011 | Murray et al. | |
| 2012/0201896 A1 | 8/2012 | Murray et al. | |
| 2012/0283831 A1 | 11/2012 | Murray | |
| 2013/0231609 A1 | 9/2013 | Slocum et al. | |
| 2013/0273017 A1 | 10/2013 | Murray | |
| 2014/0134249 A1 | 5/2014 | Murray et al. | |
| 2015/0367030 A1 | 12/2015 | Murray | |
| 2016/0206779 A1 | 7/2016 | Murray | |
| 2016/0263279 A1 | 9/2016 | Murray et al. | |
| 2017/0340772 A1 | 11/2017 | Murray | |
| 2018/0207316 A1 | 7/2018 | Murray | |
| 2019/0134569 A1 | 5/2019 | Murray | |

FOREIGN PATENT DOCUMENTS

| | | |
|---|---|---|
| EP | 0445951 A2 | 9/1991 |
| GB | 2106794 A | 4/1983 |
| SU | 733665 | 5/1980 |
| WO | WO 85/00511 A1 | 2/1985 |
| WO | WO 92/13565 A1 | 8/1992 |
| WO | WO 93/11723 A1 | 6/1993 |
| WO | WO 93/21857 A1 | 11/1993 |
| WO | WO 95/25550 A1 | 9/1995 |
| WO | WO 99/40771 A2 | 8/1999 |
| WO | WO 00/47130 * | 8/2000 |
| WO | WO 2000/74760 A2 | 12/2000 |
| WO | WO 2002/067812 A2 | 9/2002 |
| WO | WO 2003/105737 A1 | 12/2003 |
| WO | WO 2004/078134 A2 | 9/2004 |
| WO | WO 2008/036393 A1 | 3/2008 |
| WO | WO 2008/060361 A2 | 5/2008 |
| WO | WO 2008/109407 A2 | 9/2008 |
| WO | WO 2008/109807 A2 | 9/2008 |
| WO | WO 2010/048418 A1 | 4/2010 |
| WO | WO 2010/084481 A1 | 7/2010 |
| WO | WO 2010/108237 A1 | 9/2010 |

OTHER PUBLICATIONS

Kanungo et al., Density-property relationships in mineralized collagen-glycosaminoglycan scaffolds. Acta Biomater. May 2009;5(4):1006-18. doi: 10.1016/j.actbio.2008.11.029. Epub Dec. 11, 2008.

Landis et al., Collagen as a scaffold for biomimetic mineralization of vertebrate tissues. Journal of Materials Chemistry. 2006;(16):1495-1503.

Parenteau-Bareil et al., Collagen-based biomaterials for tissue engineering applications. Materials. 2010 (3):1863-1887.

(56) References Cited

OTHER PUBLICATIONS

International Search Report and Written Opinion for PCT/US2014/014141 dated May 13, 2014.
International Preliminary Report on Patentability for PCT/US2014/014141 dated Aug. 13, 2015.
International Preliminary Examination Report for PCT/US2002/023885 dated Mar. 11, 2004.
International Search Report for PCT/US2002/023885 dated Apr. 4, 2003.
Written Opinion for PCT/US2002/023885 dated Jun. 26, 2003.
Extended European Search Report for EP 06720499.0 dated Jul. 16, 2009.
International Search Report and Written Opinion for PCT/US2006/004445 dated Jul. 1, 2008.
International Preliminary Report on Patentability for PCT/US2006/004445 dated Feb. 26, 2009.
International Search Report and Written Opinion for PCT/US2007/001908 dated Oct. 31, 2007.
International Preliminary Report on Patentability for PCT/US2007/001908 dated Aug. 7, 2008.
Invitation to Pay Additional Fees for PCT/US2007/021009 dated Sep. 8, 2009.
International Search Report and Written Opinion for PCT/US2007/021009 dated Dec. 22, 2009.
International Preliminary Report on Patentability for PCT/US2007/021009 dated Jan. 21, 2010.
Extended European Search Report for EP 13743583.0 dated Sep. 17, 2015.
[No Author Listed] Guidance document for testing biodegradable polymer implant devices, Division of General and Restorative Devices, Center for Devices and Radiological Health, U.S. Food and Drug Administration (Apr. 20, 1996).
Anseth et al., "Polymerizable degradable plyanhydrides with osteocompatibility," 17(2) Nature Biotechnol. 156-159 (Feb. 1999).
Arendt and Dick, "Knee injury patterns among men and women in collegiate basketball and soccer," 23(6) Am. J. Sports Med. 694-701 (1995).
Buck, "Regeneration of Tendon," 66(1) J. Pathol. Bacteriol. 1-18 (1953).
Chamberlain et al., "Early peripheral nerve healing in collagen and silicone tube implants: myofibroblasts and the cellular response," 19 Biomaterials 1393-1403 (1998).
Chamberlain, "Collagen-GAG Substrate Enhances the Quality of Nerve Regeneration through Collagen Tubes up to Level of Autograft," 154(2) Experimental Neurology 315-329 (Dec. 1998).
Chamberlain, "Long term functional and morphological evaluation of peripheral nerves regenerated through degradable collagen implants," (M.S. Thesis, Massachusetts Institute of Technology, 1998) (file with the MIT library).
Deie et al., "High intrinsic healing potential of human anterior cruciate ligament," 66(1) Acta. Orthop. Scand. 28-32 (1995).
Desrosiers et al., "Proliferative and matrix synthesis response of canine anterior cruciate ligament fibroblasts submitted to combined growth factors," 14(2) J. Orthop. Res. 200-208 (1996).
Dye, "The Future of Anterior Cruciate Ligament Restoration," 325 Clin. Orthop. 130-139 (1996).
Faryniarz, et al., "Myofibroblasts in the healing lapine medial collateral ligament: possible mechanisms of contraction," 14(2) J. Orthop. Res. 228-237 (1996).
Ferber, "Lab Grown Organs Take Shape," 284(5413) Science 422-425 (Apr. 16, 1999).
Ferber, "Tissue Engineering: From the Lab to the Clinic," 284(5413) Science 422-425 (Apr. 16, 1999).
Ford et al., "Autologous Collagen Vocal Fold Injection: A Preliminary Clinical Study," 105 Laryngoscope 944-948 (Sep. 1995).
Frank et al., "Natural History of Healing in the Repaired Medical Collateral Ligament," 1(2) J. Orthop. Res. 179-188 (1983).
Geiger et al., "An in vitro assay of anterior cruciate ligament (ACL) and medial collateral ligament (MCL) cell migration," 30(3) Connect Tissue Res. 215-224 (1994).
Gerich et al., Gene transfer to the patellar tendon, Knee Surg, Sports Traumatol, Arthroscopy (1997) 5:118-123.
Gwinn et al., "Relative general incidence of anterior cruciate ligament injury at a military service academy," 66th Annual Meeting of Amer. Acad. of Orthop. Surg., Anaheim, California (1999).
Hefti et al., "Healing of the Transected Anterior Cruciate Ligament in the Rabbit," 73A (3) J. Bone Joint Surg. 373-383 (Mar. 1991).
Jackson et al., "Biologic remodeling after anterior cruciate ligament reconstruction using a collagen matrix derived from demineralized bone: an experimental study in the goat model," 24(4) Am. J. Sports Med. 405-414 (Jul.-Aug. 1996).
Juncosa-Melvin et al., The effect of autologous mesenchymal stem cells on the biomechanics and histology of gel-collagen sponge constructs used for rabbit patellar tendon repair. Tissue Eng. Feb. 2006;12(2):369-79.
Kato et al., "Formation of continuous collagen fibres: evaluation of biocompatibility and mechanical properties," 11 Biomaterials 169-175 (Apr. 1990).
Kawamoto et al., "Selective migration of alpha-smooth muscle actin-positive myofibroblasts toward fibronectin in the Boyden's blindwell chamber," 93(4) Clin. Sci. 355-362 (1997).
Louie, "Effect of a porous collagen-glycosaminoglycan copolymer on early tendon healing in a novel animal model," (Ph.D. Thesis, Massachusetts Institute of Technology, 1997) (file with the MIT Library).
Louie et al., "Development of a collagen-GAG copolymer implant for the study of tendon regeneration," M331 Mat. Res. Soc. Symp. Proc. 19-24 (1994).
Louie et al., "Healing of tendon defects implanted with a porous collagen-GAG matrix: histological evaluation," 3(2) Tissue Eng'g 187-195 (1997).
Marshall et al., "The Anterior Cruciate Ligament: A Technique of Repair and Reconstruction," 143 Clin. Orthop. 97-106 (Sep. 1979).
Masur et al., "Myofibroblasts differentiate from fibroblasts when plated at low density," 93(9) Proc. Nat'l Acad. Sci. USA 4219-4223 (Apr. 1996).
Murray et al., "Differences in the outgrowth of cells from explants from the proximal and distal human ACL and response to TGF-B1," Transactions of the 47th Annual Meeting of the Orthopaedic Research Society, Feb. 2001. 25-28; San Francisco, CA.
Murray et al., "Fibroblast distribution in the anteriomedial bundle of the human anterior cruciate ligament: The presence of alpha smooth muscle actin-positive cells," 17(1) J. Orthop. Res. 18-27 (1999).
Murray et al., "Histological changes in the human anterior cruciate ligament after rupture," 82A(10) J. Bone Joint Surg. 1387-1397 (2000).
Murray et al., "Migration of cells from human anterior cruciate ligament explants into collagen-glycosaminoglycan scaffolds," 18(4) J. Orthop. Res. 557-564 (2000).
Murray et al., "Migration of cells from ruptured human anterior cruciate ligament explants into collagen-GAG matrices," Proceedings of the Sixth World Biomaterials Congress, 2000; Kamuela, Hawaii.
Murray et al., "Migration of human anterior cruciate ligament fibroblasts into porous collagen-GAG matrices in vitro," 24th Annual Meeting of the Society for Biomaterials, Apr. 22-26, 1996, San Diego, CA p. 463.
Murray et al., "The effect of ruptured human anterior cruciate ligament histology on cell interactions with a CG scaffold," Davos Tissue Engineering Workshop, 2000; Davos, Switzerland.
Murray et al., "The effects of selected growth factors on human ACL cell interactions with 3-D collagen-GAG scaffolds," Transactions of the 47th Annual Meeting of the Orthopaedic Research Society, Feb. 25-28, 2001; San Francisco, CA.
Murray et al., "The migration of cells from the ruptured human anterior cruciate ligament into collagen-glycosaminoglycan regeneration templates in vitro," 22 Biomat. 2393-2402 (2001).
Murray et al., "The migration of human anterior cruciate ligament fibroblasts into porous collagen-GAG matrices in vitro," 45th Annual Meeting, Orthopedic Research Society, Anaheim, California (Feb. 1-4, 1999).

(56) References Cited

OTHER PUBLICATIONS

Murray, M.M., et al., Use of a collagen-platelet rich plasma scaffold to stimulate healing of a central defect in the canine ACL, J Orthop Res. Apr. 24, 2006(4):820-30.

Nakamura et al., A comparison of in vivo gene delivery methods for antisense therapy in ligament healing, Gene Therapy (1998) 5: 1455-1461.

Nakamura et al., Early biological effect of in vivo gene transfer of platelet-derived growth factor (PDGF)-S into healing patellar ligament, Gene Therapy (1998) 5: 1165-1170.

Niklason et al., "Functional arteries grown in vitro," 284(5413) Science 489-493 (Apr. 16, 1999).

Noyes et al., Bone-patellar ligament-bone and fascia lata allografts for reconstruction of the anterior cruciate ligament. J Bone Joint Surg Am. Sep. 1990;72(8):1125-36.

Peter et al., "Synthesis of poly(propylene fumarate) by acylation of propylene glycol in the presence of a proton scavenger," 10(3) J. Biomater. Sci. Polym. Ed. 363-373 (1999).

Schmidt et al., "Effect of growth factors on the proliferation of fibroblasts from the medial collateral and anterior cruciate ligaments," 13(2) J. Orthop. Res. 184-190 (1995).

Spindler et al., "Comparison of collagen synthesis in the peripheral and central region of the canine meniscus," 303 Clinical Orthopaedics 256-263 (Jun. 1994).

Spindler et al., "Patellar tendon and anterior cruciate ligament have different mitogenic responses to platelet-derived growth factor and transforming growth factor Beta," 14(4) J. Orthop. Res. 542-546 (1996).

Spindler et al., "Regional mitogenic response of the meniscus to platelet-derived growth factor (PDGF-AB)," 13(2) J. Orthop. Res. 201-207 (1995).

Stevenson, "Gender differences in knee injury epidemiology among competitive alpine ski racers," 18 Iowa Orthop. J. 64-66 (1998).

Stone et al., "Future Directions: Collagen-Based Prostheses for Meniscal Regeneration," 252 Clinical Orthopaedics and Related Research 129-135 (Mar. 1990).

Stone et al., "Regeneration of Meniscal Cartilage with Use of a Collagen Scaffold," 79A(12) J. Bone and Joint Surg. 1770-1777 (Dec. 1997).

Suggs et al., "Platelet adhesion on a bioresorbable poly(propylene fumarate-co-ethylene glycol) copolymer," 20(7) Biomaterials 683-690 (1999).

Torres, "Effects of modulus of elasticity of collagen sponges on their cell-mediated contraction in vitro," M. S. Thesis, Massachusetts Institute of Technology (1998) (file with the MIT Library).

Troxel, "Delay of skin wound contraction by porous collagen-GAG matrices," (Ph. D. Thesis, Massachusetts Institute of Technology, 1994) (on file with the MIT Library).

Weadock et al., "Physical crosslinking of collagen fibers: comparison of ultraviolet irradiation and dehydrothermal treatment," 29 J. Biomed. Mater. Res. 1373-1379 (1995).

Witkowski et al., "Migration and Healing of Ligament Cells under Inflammatory Conditions," 15(2) J. Orthop. Res. 269-277 (1997).

Yannas, Regeneration of Skin and Nerve by Use of Collagen Templates. Collagen Volume 3, Chapter 4, Biotechnology, Nimni Ed., p. 87-115 (CRC Press, Boca Raton, Florida, 1989).

Yannas, "Models of Organ Regeneration Processes Induces by Templates," Bioartificial Organs: Science, Medicine, and Technology, Prokop et al. Ed., pp. 280-293 (The New York Academy of Sciences, New York, NY 1997).

Yannas, et al., "Polymeric template facilitates regeneration of sciatic nerve across 15-millimeter gap," 8 Trans. Soc. Biomater. 146 (1985).

Yannas et al., "Synthesis and characterization of a model extracellular matrix that induces partial regeneration of adult mammalian skin," 86 Proc. Natl. Acad. Sci USA 933-937 (Feb. 1989).

Supplementary Partial European Search Report for EP 14745975.4 dated Aug. 26, 2016.

Extended European Search Report for EP 14745975.4 dated Jan. 31, 2017.

Kliment et al., A novel method for accurate collagen and biochemical assessment of pulmonary tissue utilizing one animal. Int J Clin Exp Pathol. Apr. 2011;4(4):349-55.

Neuman et al., The determination of hydroxyproline. J Biol Chem. May 1950;184(1):299-306.

Foster et al., Platelet-rich plasma: from basic science to clinical applications. Am J Sports Med. Nov. 2009;37(11):2259-72. doi: 10.1177/0363546509349921.

Stenzel et al., Collagen as a biomaterial. Annu Rev Biophys Bioeng. 1974;3(0):231-53.

Australian Examination Report for Application No. 2017254864 dated Aug. 31, 2018.

[No Author Listed] Merriam Webster Dictionary Definition. Carbonate-apatite. Retrieved on Jan. 5, 2019.

Abdalmula et al., Clinical and histopathological characterization of a large animal (ovine) model of collagen-induced arthritis. Vet Immunol Immunopathol. May 15, 2014;159(1-2):83-90.

Abdalmula et al., Immunoselected STRO-3(+) mesenchymal precursor cells reduce inflammation and improve clinical outcomes in a large animal model of monoarthritis. Stem Cell Res Ther. Feb. 7, 2017;8(1):22.

Bakker et al., C3-Tat/HIV-regulated intraarticular human interleukin-1 receptor antagonist gene therapy results in efficient inhibition of collagen-induced arthritis superior to cytomegalovirus-regulated expression of the same transgene. Arthritis Rheum. Jun. 2002;46(6):1661-70.

Brand et al., Collagen-induced arthritis. Nat Protoc. 2007;2(5):1269-75.

Cross et al., Dense type I collagen matrices that support cellular remodeling and microfabrication for studies of tumor angiogenesis and vasculogenesis in vitro. Biomaterials. Nov. 2010;31(33):8596-607.

Del Conde et al., Platelet activation leads to activation and propagation of the complement system. J Exp Med. Mar. 21, 2005;201(6):871-9.

Dooley et al., Endothelial dysfunction in an ovine model of collagen-induced arthritis. J Vasc Res.2014;51(2):90-101.

Itoh et al., Characterization of CO3Ap-collagen sponges using x-ray high-resolution microtomography. Biomaterials 25. 2004:2577-2583.

Kaufmann, Immunology's foundation: the 100-year anniversary of the Nobel Prize to Paul Ehrlich and Elie Metchnikoff. Nat Immunol. Jul. 2008;9(7):705-12. Abstract Only.

Lee et al., Suppression of the onset and progression of collagen-induced arthritis by chebulagic acid screened from a natural product library. Arthritis Rheum. Jan. 2005;52(1):345-53.

Lee et al., The establishment of a porcine rheumatoid arthritis model: Collagen induced arthritis minipig model. J Pharmacol Sci. Sep. 2016;132(1):41-47.

Lubberts et al., Intra-articular IL-10 gene transfer regulates the expression of collagen-induced arthritis (CIA) in the knee and ipsilateral paw. Clin Exp Immunol. May 2000;120(2):375-83. vol. 1.

Lubberts et al., IL-1-independent role of IL-17 in synovial inflammation and joint destruction during collagen-induced arthritis. J Immunol. Jul. 15, 2001;167(2):1004-13. vol. 2.

Peerschke et al., Blood platelets activate the classical pathway of human complement. J Thromb Haemost. Sep. 2006;4(9):2035-42.

Peerschke et al., Complement activation on platelets: implications for vascular inflammation and thrombosis. Mol Immunol. Aug. 2010;47(13):2170-5.

Qiu et al., Outgrowth of chondrocytes from human articular cartilage explants, and expression of alpha-smooth muscle actin, 18 Wound Repair and Regeneration 383-391 (Sep.-Oct. 2000).

Shen et al., Simiao Pill Attenuates Collagen-Induced Arthritis in Rats through Suppressing the ATX-LPA and MAPK Signalling Pathways. Evid Based Complement Alternat Med. Mar. 14, 2019;2019:7498527.

Silawal et al., Osteoarthritis and the Complement Cascade. Clin Med Insights Arthritis Musculoskelet Disord. Jan. 3, 2018;11:1179544117751430.

(56) References Cited

OTHER PUBLICATIONS

Thompson et al., An Experimental Study of the Bacteriolytic Complement Content of the Blood Serum in Normal, Vaccinated, and Variolated Rabbits. J Med Res. Aug. 1903;10(1):63-70.
Thorp et al., Type II collagen-immune complex arthritis in sheep: collagen antibodies in serum, synovial fluid and afferent lymph. Clin Exp Rheumatol. Mar.-Apr. 1992;10(2):143-50.
Wang et al., Comparative Evaluation of (68)Ga-Citrate PET/CT and (18)F-FDG PET/CT in the Diagnosis of Type II Collagen-Induced Arthritis in Rats. Contrast Media Mol Imaging. Mar. 19, 2019;2019:2353658.
Cameron et al., "The natural history of the anterior cruciate ligament-deficient knee: changes in synovial fluid cytokine and keratan sulfate concentrations," The American Journal of Sports Medicine, Nov. 1997, 25(6):751-4.
Yamashita et al., "Tracheal regeneration after partial resection: a tissue engineering approach," The Laryngoscope, Mar. 2007, 117(3):497-502.
Ahn et al., "New bone formation following sinus membrane elevation without bone grafting: histologic findings in humans," International Journal of Oral & Maxillofacial Implants, Jan. 1, 2011, 26(1).

\* cited by examiner

A

B

A.

B.

C.

A.

B

C

A

B

C

C.

BIOMATERIAL FOR ARTICULAR CARTILAGE MAINTENANCE AND TREATMENT OF ARTHRITIS

This application is a national stage filing under U.S.C. § 371 of PCT International application PCT/US2013/024467, filed Feb. 1, 2013, which claims priority under 35 U.S.C. § 119(e) to U.S. Provisional Application Ser. No. 61/593,415, entitled "BIOMATERIAL FOR ARTICULAR CARTILAGE MAINTENANCE" filed on Feb. 1, 2012, which is herein incorporated by reference in its entirety.

GOVERNMENT SUPPORT

This invention was made with government support under grant number AR056834 awarded by the National Institutes of Health. The Government has certain rights in the invention.

FIELD OF THE INVENTION

This invention relates generally to biomaterials and methods for maintaining articular cartilage health, preventing or reducing progression of cartilage damage, and alleviating and/or reducing the risk for developing arthritis.

BACKGROUND INFORMATION

Articular cartilage in human joints often undergoes a steady process of deterioration, cumulating in osteoarthritis in the later decades of life. Small injuries typically do not heal, but progress to further injury. In addition, after an injury to other tissues within the joint, for example, the anterior cruciate ligament (ACL), the articular cartilage has an accelerated pace of deterioration, leading to post-traumatic arthritis within 15 years of the original injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid, which, as part of normal joint activity, naturally prevent clot formation in joints. This fibrinolytic process results in premature degradation of the fibrin clot scaffold and disruption of the healing process for tissues within the joint or within intra-articular tissues and progression of even minor injuries inevitably ensues.

The current treatment method for cartilage maintenance is weight bearing exercise, with other treatments such as oral supplements (e.g., chondroitin sulfate/GAG), or injections of proteins like hyaluronic acid or lubricin for treatment of established injuries. To date, there has been no effective treatment for preventing the deterioration of articular cartilage after an intra-articular injury. The loss of ACL function has been found to result in early and progressive radiographic changes consistent with joint deterioration (Hefti et al., 73A(3) *J. Bone Joint Surg.* 373-383 (1991)). As ACL rupture is most commonly an injury of young athletes, early osteoarthritis in this group has difficult consequences.

SUMMARY OF INVENTION

Anterior cruciate ligament rupture, a most common injury of young athletes, is associated with early osteoarthritis, which has difficult consequences. The present disclosure is based on the unexpected discoveries that biomaterials (e.g., collagen materials) as described herein, can alleviate and/or reduce the risk for developing arthritis, particularly post-traumatic arthritis (e.g., osteoarthritis associated with ACL rupture or arthritis associated with arthroscopic surgery). Accordingly, provided herein are biomaterials and methods for treating, minimizing development of, and/or inhibiting arthritis (e.g., osteoarthritis) following trauma or injury to a joint, such as an ACL tear, meniscal injury, minor cartilage injury, or joint surgery. The therapeutic interventions described herein that minimize development of arthritis (e.g., osteoarthritis) offer several advantages over the current standard of care, i.e., merely limiting impact activity and subsequent treatment of chondral lesions that develop. By reducing and/or preventing progression of injury to a damaged tissue, the complex morphology and architecture of the hyaline cartilage can be preserved, as well as the biochemical makeup of cartilage—two key features which govern articular cartilage performance and until now, as described herein, have not been able to be restored with treatment of an established chondral defect.

One aspect of the present disclosure features a method for treating arthritis (e.g., osteoarthritis, rheumatoid arthritis, or psoriatic arthritis), comprising administering (e.g., via direct injection or surgical implantation) to a joint of a subject that has or is at risk for developing arthritis at the joint an effective amount of a collagen material (a composition comprising collagen), which can comprise at least one or more of the following: a growth factor, calcium, a platelet, a white blood cell, a stem cell, a cross-linker, or a neutralizing agent; wherein the subject is not concurrently surgically treated to repair a torn or ruptured intra-articular tissue.

In some embodiments, the arthritis is post-traumatic arthritis such as arthritis associated with an intra-articular injury or arthroscopic surgery. Exemplary intra-articular injuries include, but are not limited to, anterior cruciate ligament tear, anterior cruciate ligament rupture, meniscal injury, and cartilage injury.

In other embodiments, the subject was surgically treated for a torn, fractured, strained, bruised, or ruptured intra-articular tissue at the joint, which can be a joint of hand, elbow, wrist, hip, knee, foot, shoulder, ankle, temporomandibular, or spine, at least one day prior to the administration of the collagen material. The subject can have an injury associated with the development of arthritis.

Another aspect of the present disclosure features a method for reducing the risk for developing arthritis, comprising administering to a subject having an acute joint injury, by direct injection or surgical implantation, into a joint (e.g., a joint of hand, elbow, wrist, hip, knee, foot, shoulder, ankle, temporomandibular, or spine) where the acute joint injury occurs, an effective amount of a collagen material, which can comprise at least one or more of the following: a growth factor, calcium, a platelet, a white blood cell, a stem cell, a cross-linker, or a neutralizing agent. In one example, the subject can be a subject surgically treated for a torn, fractured, strained or bruised or ruptured intra-articular tissue at the joint at least one day prior to the administration of the collagen material. In some examples, the collagen material can be a fiber, powder, sponge or gel. It may be solid, liquid, or dry powder. In one example, the collagen material described herein contains only collagen.

In some embodiments of these aspects and all such aspects described herein, the subject to be treated by any of the methods described herein can be a mammal. The mammal can be, e.g., a human, non-human primate, mouse, rat, dog, cat, horse, or cow. In one example, the subject is an adolescent subject. In another example, the subject is a young athlete.

The collagen material such as collagen gel, sponge, fibers or powder used in any of the methods described herein comprises collagen. The collagen material can contain only collagen. Alternatively, it can further comprise a non-collagen extracellular matrix component, a platelet, and/or calcium. In some examples, the collagen material further comprises a platelet and a neutralizing agent, e.g. sodium hydroxide or hydrochloric acid. In other examples, the collagen material further comprises a platelet and calcium. In some examples, the platelet is derived from the subject. In other examples, the platelet is derived from a donor that is allogeneic to the subject. The collagen material described herein can additionally include plasma. In some embodiments, the plasma is derived from the subject to which any of the methods described herein is to be performed. In other embodiments, the plasma is derived from a donor that is allogeneic to the subject. In some embodiments, a collagen gel can be freeze-dried or lyophilized and delivered as a powder, scaffold or sponge. In some embodiments, the collagen can be processed into a collagen fiber. In some embodiments, the collagen fiber can be formed by spinning, electrospinning, exposure to temperature gradients or other methods of directed fiber formation. In some embodiments, the gel can be partially lyophilized to increase the concentration of collagen or other materials within the gel.

Any of the collagen materials described herein can be formulated for the administration to a patient, e.g., via direct injection, to a joint where treatment is needed. The collagen materials provided herein are suitable for administration to a subject having or having had an injury or trauma to a joint, such as an ACL injury.

The collagen in any of the collagen gels described herein can be of the soluble or the insoluble type. Preferably, the collagen is soluble, e.g., acidic or basic. For example the collagen can be type I, II, III, IV, V, IX or X. In some preferred embodiments, the collagen is soluble. More preferably the collagen is soluble type I collagen. In some embodiments, the collagen material described herein comprises a mixture of soluble and insoluble collagen. In some embodiments, the collagen is capable of self-assembly into larger units or fibers of collagen.

In some embodiments, the collagen materials described herein can further comprise one or more additional components, such as insoluble collagen, a growth factor, a cross-linking agent, a stem cell, a genetically altered fibroblast and a cell media supplement. Growth factors include, for example, platelet derived growth factor-AA (PDGP-AA), platelet derived growth factor-BE (PDGF-BB), platelet derived growth factor-AB (PDGF-AB), transforming growth factor beta (TGF-β), epidermal growth factor (EGF), acidic fibroblast growth factor (aFGF), basic fibroblast growth factor (bFGF), insulin-like growth factor-I (IGF-1), interleukin-1-alpha (IL-Ia), and insulin. Cell media supplement is meant to include for example glucose, ascorbic acid, antibiotics, or glutamine.

Any of the collagen materials described herein can be substantially free of one or more of the following: nucleic acid (DNA and/or RNA), glycosaminoglycan (GAG), phospholipid, active pepsin, and active virus. In other embodiments, the collagen material can have a substantially reduced level of one or more of the following: nucleic acid (DNA and/or RNA), glycosaminoglycan (GAG), phospholipid, active pepsin, and active virus. In one example, the content of phospholipid in the collagen material is less than 20% (e.g., less than 15%, 10%, 5%, or 1%) of that found in a native tissue. The content of phospholipid in the collagen material can be less than 10,000 μM/mg, 5,000 μM/mg, 2,500 μM/mg, 1,250 μM/mg, 1,000 μM/mg, 500 μM/mg, 125 μM/mg, or 50 μM/mg. In another example, the content of nucleic acids (e.g., DNA or RNA) in the collagen material is less than 20% (e.g., less than 15%, 10%, 5%, or 1%) of that found in a native tissue. The content of nucleic acids in the collagen material can be less than 700 μg/g, 350 μg/g, 200 μg/g, 100 μg/g, 35 μg/g, 10 μg/g, 5 μg/g, 1 μg/g, 0.5 μg/g, or 0.25 μg/g. In yet another example, the level of active pepsin in the material is less than 10,000 μg/ml (e.g., 1,000 μg/ml or 200 μg/ml). In still another example, the content of GAG in the collagen material is less than 50% of the total material (e.g., less than 40%, 30%, 20%, 10%, or 5%).

Any of the collagen materials described herein can be treated by terminal sterilization, e.g., ethylene oxide sterilization or electron beam sterilization. In some embodiments, the ethylene oxide sterilization may be conducted under specific conditions (e.g., those described in Examples below). For example, the ethylene oxide sterilization may be conducted with a cycle temperature of less than 120 degrees F., e.g., less than 110 degrees F., 100 degrees F., or 90 degrees F. Prior to the sterilization, the collagen material can be lyophilized. Alternatively or in addition, the collagen material can be rehydrated after the sterilization.

In another aspect, described herein is an extracellular matrix (ECM) material (e.g., an ECM scaffold such as a collagen scaffold), comprising at least one extracellular matrix component (e.g., collagen or a non-collagen ECM component), calcium, and optionally a platelet, wherein the content of calcium in the ECM solution for preparing the ECM scaffold ranges from 1-5 mg/g (calcium/ECM solution) or about 0.005-10 g $CaCl_2$ per gram of the ECM component (e.g., collagen), for example, 1-5 mg $CaCl_2$/40 mg ECM protein (e.g., collagen). In another embodiment, the calcium content can range from 1 to 5 gm $CaCl_2$ to each gram of collagen in the biomaterial as described herein. In another embodiment, 10 to 200 mM of calcium can be added to the collagen material or scaffold. Such an ECM scaffold can further comprise one or more of the following: growth factor, platelet, white blood cell, stem cell, cross-linker, and neutralizing agent. In some examples, the ECM scaffold is prepared from an ECM solution comprising at least 100 mOsm calcium per kilogram of collagen solution. In other examples, the ECM scaffold is prepared from an ECM solution comprising at least 90 mOsm (e.g., 80, 70, 60, 50, 40, 30, 20, or 10 mOsm) calcium per liter.

Any of the calcium-containing biomaterials, such as collagen materials, as described herein, can be substantially free of one or more of the following: nucleic acid (DNA and/or RNA), glycosaminoglycan (GAG), phospholipid, active pepsin, and active virus. In other embodiments, the collagen material can have a substantially reduced level of one or more of the following: nucleic acid (DNA and/or RNA), glycosaminoglycan (GAG), phospholipid, active pepsin, and active virus. In one example, the content of phospholipid in the collagen material is less than 20% (e.g., less than 15%, 10%, 5%, or 1%) of that found in a native tissue. The content of phospholipid in the collagen material can be less than 10,000 μM/mg, 5,000 μM/mg, 2,500 μM/mg, 1,250 μM/mg, 1,000 μM/mg, 500 μM/mg, 125 μM/mg, or 50 μM/mg. In another example, the content of nucleic acids (e.g., DNA or RNA) in the collagen material is less than 20% (e.g., less than 15%, 10%, 5%, or 1%) of that found in a native tissue. The content of nucleic acids in the collagen material can be less than 700 μg/g, 350 μg/g, 200 µg/g, 100 µg/g, 35 µg/g, 10 µg/g, 5 µg/g, 1 µg/g, 0.5 µg/g, or 0.25 µg/g. In yet another example, the level of active pepsin in the material is less than 10,000 µg/ml (e.g., 1,000 µg/ml or 200 µg/ml). In still another example, the content of GAG in the collagen material is less than 50% of the total material (e.g., less than 40%, 30%, 20%, 10%, or 5%).

In some embodiments, the biomaterial described herein (e.g., a collagen material) comprises GAG. The content of GAG in such a biomaterial can be at least 20% of the total dry weight of the biomaterial, for example, at least 30%, 40%, or 50% of the total dry weight of the biomaterial. In some examples, the GAG-containing biomaterial is substantial free of nucleic acids (e.g., DNA and/or RNA), phospholipid, active pepsin, and/or active virus as described herein. In one example, the content of phospholipid in the collagen material is less than 20% (e.g., less than 15%, 10%, 5%, or 1%) of that found in a native tissue. The content of phospholipid in the collagen material can be less than 10,000 µM/mg, 5,000 µM/mg, 2,500 µM/mg, 1,250 µM/mg, 1,000 µM/mg, 500 µM/mg, 125 µM/mg, or 50 µM/mg. In another example, the content of nucleic acids (e.g., DNA or RNA) in the collagen material is less than 20% (e.g., less than 15%, 10%, 5%, or 1%) of that found in a native tissue. The content of nucleic acids in the collagen material can be less than 700 µg/g, 350 µg/g, 200 µg/g, 100 µg/g, 35 µg/g, 10 µg/g, 5 µg/g, 1 µg/g, 0.5 µg/g, or 0.25 µg/g. In yet another example, the level of active pepsin in the material is less than 10,000 µg/ml (e.g., 1,000 µg/ml or 200 µg/ml).

In another aspect, the present disclosure provides a method for preparing extracellular matrix (ECM) scaffolds such as collagen scaffolds that comprise calcium. Such calcium-containing scaffolds are also described herein.

In some examples, the method for preparing the calcium-containing ECM scaffold comprises: mixing a composition comprising at least one ECM component (e.g., those described herein such as collagen) with a calcium solution to form a mixture; lyophilizing the mixture to form an ECM sponge (e.g., a collagen sponge); and neutralizing the ECM sponge (e.g., via a HEPES buffer) to produce the calcium-containing ECM scaffold. Optionally, the ECM sponge can be rehydrated prior to the neutralization.

In other examples, the method for preparing the calcium-containing ECM scaffold comprises: soaking an ECM sponge in a calcium solution, wherein the ECM sponge comprises at least one ECM component (e.g., those described herein such as collagen) and is neutralized; and lyophilizing the ECM sponge to form the calcium-containing ECM scaffold. The method can further comprise the following steps for preparing the ECM sponge (e.g., collagen sponge): neutralizing a slurry containing at least one ECM component such as collagen to form a neutralized ECM slurry (e.g., collagen slurry); incubating the neutralized ECM slurry to allow gelation of the slurry; and lyophilizing the ECM material (e.g., collagen material) thus formed to produce the ECM sponge. Prior to the neutralizing step, the method can further comprise: lyophilizing an ECM solution (e.g., a collagen solution); and rehydrating the lyophilized ECM solution to form the ECM slurry.

In any of the methods for preparing the calcium-containing ECM scaffold described herein, the calcium solution can have a calcium concentration of about 30 mM to 90 mM. Alternatively or in addition, the ratio of calcium to collagen is about (0.005-10):1 (by weight).

In some aspects, provided herein are methods of inhibiting or preventing development or progression of arthritis, or reducing the risk for developing arthritis, in a subject having or having had an injury (e.g., those described herein) or trauma to an articular joint. The method comprises placing (e.g., via direct injection) any of the collagen materials and/or ECM scaffolds described herein, within the injured articular joint. Such methods help prevent or inhibit progression of arthritis in the injured articular joint, thereby providing the subject with increased mobility and reduced risk of need for subsequent surgeries to the joint.

In some aspects, provided herein are methods of preventing or inhibiting the progression of an injury in a subject (e.g., any of those described herein), by placing a biomaterial as described herein (e.g., a collagen material such as collagen gel or collagen sponge, or an ECM scaffold containing calcium) within an intra-articular space after an injury. Such methods help prevent or inhibit progression of injury in the damaged tissue directly (e.g., to prevent or inhibit progression of a partial ACL injury to a complete injury), as well as minimize progression of injury to associated tissue (e.g., to minimize progression of articular cartilage injury after an ACL tear). Intra-articular injuries include, but are not limited to, for example, a meniscal tear, ligament tear, bone bruise, or a cartilage lesion.

Also provided herein are methods of preventing or inhibiting progression of an extra-articular injury in a subject, by placing a biomaterial (e.g., a collagen material, which may contain calcium) as described herein adjacent to an extra-articular structure. Extra-articular injuries include, for example, injuries of the ligament, tendon, bone or muscle.

In some embodiments of the methods described herein, the methods further comprise mechanically joining the ends of the injured tissue, e.g., suturing.

Also provided herein, in some aspects, are biomaterials such as collagen materials or ECM materials, and methods for promoting a coating for an injured tissue and tissues in the same joint, and increasing or stimulating migration of appropriate healing cells to support and reinforce the injured tissues and those tissues that have changes in their biomechanical performance as the result of injury of adjacent tissues. Such devices act as bioengineered substitute or substitute scaffolds for fibrin clot and are implanted within an intra-articular space. Such substitute scaffolds are designed to stimulate cell proliferation and extracellular matrix production into intra-articular tissues, thus facilitating healing and regeneration. The devices described herein resist premature degradation of the replacement clot by the intra-synovial environment.

In some embodiments of the aspects described herein, a collagen-based glue can be used as an adhesive to coat intra-articular surfaces of the meniscus, cartilage or labrum of a joint. The surfaces can be pretreated to expose selected extracellular matrix components in the meniscus. Then, the glue can be introduced into the joint. Bonds are formed between the extracellular matrix of in the meniscal tissue and the material of the glue. The bonds form a protective coating over the meniscus. This coating can then induce the migration of cells to reinforce the meniscus, which is then remodeled by cells, thus minimizing the development and progression of injury.

In some aspects, provided herein are collagen-based scaffolds for use as an adhesive, e.g. tissue-adhesive compositions (as well as a cell migration inducer) to coat intra-articular surfaces of cartilage. The cartilage can be pretreated to expose extracellular matrix components in the cartilage. A collagen scaffold (e.g. tissue-adhesive composition) can then be introduced into the joint. Bonds are formed between the extracellular matrix of the cartilage and the biomaterial, which is then remodeled by cells, thus minimizing the development and progression of injury.

In some aspects, provided herein are collagen-based scaffolds for use as an adhesive, e.g. tissue-adhesive composition (as well as a cell migration inducer) to coat intra-articular surfaces of ligaments or tendons. The ligament or tendon can be pretreated to expose extracellular matrix components in ligaments or tendons. A collagen scaffold (e.g. tissue-adhesive composition) is then introduced into the joint. Bonds are formed between the extracellular matrix of the ligament or tendon and the biomaterial, which is then remodeled by cells, thus minimizing the development and progression of injury.

In some aspects, provided herein are collagen-based scaffolds for use as an adhesive, e.g. tissue-adhesive composition (as well as a cell migration inducer) to coat intra-articular surfaces of labrum. The ligament can be pretreated to expose extracellular matrix components in the labrum. A collagen scaffold (e.g. tissue-adhesive composition) is then introduced into the joint. Bonds are formed between the extracellular matrix of the labrum and the biomaterial, which is then remodeled by cells, thus minimizing the development and progression of injury.

Also within the scope of this disclosure are (a) pharmaceutical compositions for use in treating joint injury, treating arthritis such as post-traumatic arthritis, reducing the risk for developing arthritis, and/or delaying or preventing the onset of arthritis, the pharmaceutical composition comprising any of the biomaterials (e.g., collagen materials such as collagen gels, powers, sponges, or scaffold; and ECM scaffold), and (b) uses of the just-described pharmaceutical composition in manufacturing a medicament for the noted purposes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the aspects and embodiments of the invention described herein will be apparent from the following detailed description, and from the claims.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated by reference herein for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DETAILED DESCRIPTION

Figure 1:
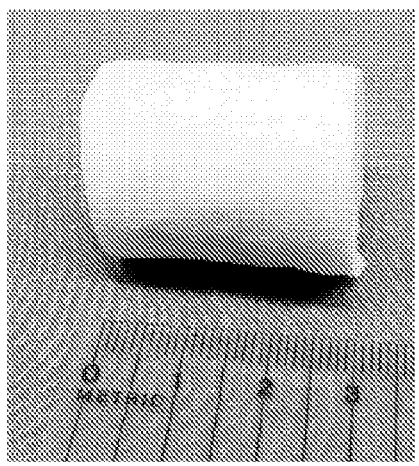
FIG. 1 is a photograph of a biomaterial that showed the property of preventing articular cartilage damage after an ACL tear. Panel A depicts a photograph of a structural member, to which a biological agent, such as platelet-rich plasma can be added to form the biomaterial. Panel B shows an example of the biologic agent, platelet-rich plasma.
Figure 1:
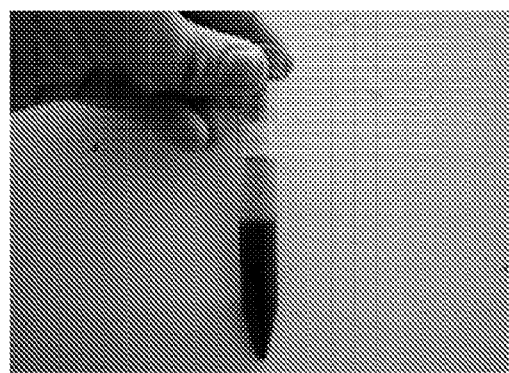

Articular cartilage in human joints often undergoes a steady process of deterioration, cumulating in osteoarthritis (also known as degenerative arthritis) in the later decades of life. Small injuries typically do not heal, but progress to further injury. Injury to the joint frequently produces an inflammatory response within the joint space that involves the synovial tissue and leads to degradation of articular cartilage, which is a symptom of osteoarthritis. Dramatic shifts in synovial and cartilage metabolism of the human knee have been described following joint injury and arthroscopic surgery (Cameron, M. L. et al., supra (1994) Cameron, M. L. et al., Am. J. Sports Med. 25:751-754 (1997)). Specific pro-inflammatory cytokine levels increase dramatically (up to 2-4 orders of magnitude) in knee joint synovial fluids during the acute inflammatory phase seen after anterior cruciate ligament (ACL) rupture. Significant changes also occur in concentrations of cartilage matrix molecules due to overproduction of matrix metalloproteinases (MMPs), such as collagenase and stromelysin-1, which are elevated in the synovial fluid of patients after acute trauma (Lohmander, L. S. et al., J. Orthopaedic Res. 12:21-28 (1994)). Temporally, the changes in cytokines and cartilage matrix markers (e.g., proteoglycans) in synovial fluid, which are correlated with cartilage degeneration, are maximal in the acute injury period but persist for extended periods (3 months to one year), declining slowly and remaining greater than preinjury baseline levels.

Trauma due to joint surgery such as arthroscopic surgery itself causes significant post-surgical inflammation that reflects additional inflammatory activation of cells in the joint, including upregulation of cyclooxgenase-2 and other pro-inflammatory cytokines. Such inflammatory responses lead to the development of arthritis.

A significant proportion (60-90%) of patients with rupture of the ACL shows radiographic changes of the knee indicative of osteoarthritis (OA) 10-15 years after injury (Cameron, M. L. et al., supra (1994)). Thus, the combined effects of initial joint injury and surgical trauma may induce a sustained inflammatory state and associated changes in cartilage matrix metabolism which appear to be causative factors resulting in the subsequent development of degenerative changes in articular cartilage and early development of osteoarthritis. The magnitude of this health problem is substantial since the total estimated number of arthroscopic procedures performed in the United States alone in 1996 was 1.8 million with an estimated growth rate of approximately 10% per annum.

Collagen was known in the art to induce arthritis when injected into a joint. As such, animal models of osteoarthritis commonly involve injection of collagen into the knees of the experimental animals to induce cartilage damage and arthritis.

The present disclosure is based on the unexpected discoveries that the collagen materials as described herein not only alleviate joint injury but also alleviate or reduce the risk for developing arthritis (e.g., osteoarthritis) associated with joint injury. Accordingly, provided herein are biomaterials such as collagen materials (e.g., collagen gel, collagen powder, collagen fiber or collagen sponge) and extracellular matrix (ECM) scaffolds, all of which may contain calcium, and methods thereof for preventing and inhibiting development and progression of injuries to intra- and extra-articular tissue, such as cartilage degeneration, and/or for treating arthritis (e.g., osteoarthritis) associated with joint injuries, e.g., trauma or surgery to the joint. For example, the biomaterials provided herein can be used in the treatment of many tissues within articular joints, including the anterior cruciate ligament, knee meniscus, glenoid labrum, and acetabular labrum. Additionally, the biomaterials and methods described herein can be used to repair bone fractures, especially where the bone fractures are located in an intra-articular environment. The biomaterials described herein are also useful for reducing, inhibiting, or preventing destruction of articular cartilage in a joint, following, for example, trauma or injury to the joint.

Definitions

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder, or the predisposition toward the disease or disorder. The term "treating" includes reducing or alleviating at least one adverse effect or symptom of a condition, disease or disorder associated with, for example, cartilage damage, such as osteoarthritis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of or at least slowing of progress or worsening of symptoms that would be expected in absence of treatment. Beneficial or desired clinical results include, but are not limited to, alleviation of one or more symptom(s) of cartilage damage, diminishment of extent or progression of arthritis development, stabilized (i.e., not worsening) state of cartilage injury, delay or slowing of progression of a cartilage injury, amelioration or palliation of the state of an injured joint, and healing or remission of a cartilage injury (whether partial or total), whether detectable or undetectable. The term "treatment" of a disease also includes providing relief from the symptoms or side-effects of the disease (including palliative treatment).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level.

The term "cartilage defect" or "cartilage degeneration" refers to any cartilage abnormality including cartilage diseases, and alteration of cartilage caused e.g. by trauma or degenerative processes.

The term "degenerative diseases" means diseases or defects with impaired cartilage structure, such as cartilage degeneration or destruction with or without involvement of bony structures. Preferably, degenerative diseases are degenerative cartilage diseases. These include, but are not limited to, osteoarthritis, temporomandibular joint disorder (TMDs), acetabular labrum disorders, arthritis, rheumatoid arthritis, psoriatic arthritis, juvenile chronic arthritis, rhizomelic pseudoarthritis, rheumatoid polyarthritis, degenerative disc disease, osteochondral defects, superficial chondral defects, osteochondritis dissecans, full-thickness chondral defects, partial-thickness chondral defects, meniscus tears, anterior crucial ligament injury, synovial osteochondromatosis, ankylosing spondylitis, synovitis, and villonodulat synovitis.

"Articular cartilage" covers the surface of the portion of bones in joints and functions as a cushion between two bones to allow movement in joints. Normal healthy cartilage is described as hyaline cartilage. Articular cartilage comprises specialized cells (chondrocytes) embedded into a matrix of intracellular material rich in proteoglycans, predominantly aggrecan, collagen type II fibrils, other proteins and water. The matrix is produced and maintained by the chondrocytes embedded within. Cartilage tissue is not innervated and vascularised and is nourished by the underlying tissue.

"Post-traumatic arthritis" as used herein refers to arthritis caused by the wearing out of a joint that has had any kind of physical injury or joint surgery such as arthroscopic surgery. The injuries, which may damage the cartilage and/or bone, can be from sports, an accident such as a vehicle accident or a fall, a military injury, or any other source of physical trauma. Exemplary intra-articular injuries include, but are not limited to, an injury to the anterior cruciate ligament (e.g., anterior cruciate ligament tear or anterior cruciate ligament rupture), an injury to knee meniscus, glenoid labrum, acetabular labrum, rotator cuff tendon, an injury to cartilage, or any combination thereof. Post-traumatic arthritis can also be arthritis associated with joint surgery such as arthroscopic surgery, which may cause local inflammation and/or infection, leading to arthritis.

A "cross-linking agent" or "cross-linker" refers to an agent is capable of forming chemical bonds between the constituents of the biomaterials described herein. The cross-linking agent or cross-linker can be, for example, a protein or a small molecule, e.g., glutaraldehyde or alcohol.

The term "subject," as used herein, refers to a mammal, for example, a primate, a non-human primate, a human, a dog, a cat, a sheep, a goat, a cattle, a horse, a pig, a mouse, a rat, a guinea pig, a domestic animal, a wild animal, a farm animal, or a laboratory animal. In some examples, the subject is an infant, e.g., a neonatal infant. In other examples, the subject is an adolescent or an adult. Other developmental stages, for example prenatal and perinatal stages are also included in some embodiments.

The terms "xenogeneic" and "xenograft" refer to cells or tissue which originates with or is derived from a species other than that of the recipient. Alternatively the collagen may be obtained from autologous cells. For instance, the collagen may be derived from a patient's fibroblasts which have been cultured. The collagen may then be used in that patient or other patients.

The terms "autologous" and "autograft" refer to tissue or cells which originate with or are derived from the recipient, whereas the terms "allogeneic" and "allograft" refer to cells and tissue which originate with or are derived from a donor of the same species as the recipient.

As used herein the term, "Type I collagen" is characterized by two α1 (I) chains, and one α2(I) chains (heterotrimeric collagen). The α1(I) chains are approximately 300 nm long. Type I collagen is predominantly found in bone, skin (in sheet-like structures), and tendon (in rope-like structures). Type I collagen is further typified by its reaction with the protein core of another connective tissue component known as a proteoglycan. Type I collagen contains signaling regions that facilitate cell migration.

A composition that is "substantially free of a component" as used herein shall mean a composition containing at most a trace amount of the component.

"An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. In the case of treating arthritis or reducing the risk for developing arthritis, the desired response is inhibiting the progression of the disease, delaying onset of the disease, or preventing occurrence of the disease. This may involve only slowing the progression of the disease temporarily, although more preferably, it involves halting the progression of the disease permanently. This can be monitored by routine methods.

Described herein are biomaterials such as collagen materials (a composition comprising collagen such as a collagen gel, collagen powder, collagen fiber or a collagen sponge), and ECM scaffolds (a scaffold that contains at least one ECM components as those described herein), which are useful in treating intra- and extra-articular injuries in a subject, e.g., a mammal such as a human patient, by contacting the ends of an injured or vulnerable tissue from the subject with the biomaterials described herein. Intra-articular injuries include for example, meniscal tears, ligament tears and cartilage lesion. Extra-articular injuries include for examples injuries to the ligament, tendon or muscle. Such biomaterials are also useful in treating or reducing the risk for arthritis (e.g., osteoarthritis) associated with joint injury and/or joint surgery.

Further, the biomaterials described herein can prevent and/or inhibit progression of connective tissue degeneration, thereby effective in treating a degenerative disease, e.g., those described herein. Prevention of deterioration offers several advantages over end stage treatment of damaged or lost tissues, including maintenance of the complex architecture of the tissues, and preservation of remaining proprioceptive fibers within the tissue substance. The present disclosure provides a scaffold (e.g., an ECM scaffold such as a collagen scaffold) which the patient's body can develop a network of capillaries, arteries, and veins. Well-vascularized connective tissues heal as a result of migration of fibroblasts into the scaffold. Such a scaffold also permits the re-enervation of the damaged area by providing a cellular substrate for regenerating neurons.

Porous collagen scaffolds of varying composition and architecture have been researched as templates for regeneration of a variety of tissues including bone, skin and muscle. A porous collagen-glycosaminoglycan (CG) scaffold has been used successfully in regeneration of dermis (Yannas et al., 86 Proc. Natl. Acad. Sci. USA 933-937 (1989)) and peripheral nerve (Chamberlain, Long Term Functional And Morphological Evaluation Of Peripheral Nerves Regenerated Through Degradable Collagen Implants (Massachusetts Institute of Technology, 1998)). Recent work has focused on the use of collagen fibers, to serve as scaffolds for the regeneration of the anterior cruciate ligament. The current design of these prostheses is as a substitute for the entire anterior cruciate ligament, that is the ruptured anterior cruciate ligament is removed from the knee and replaced by a point-to-point collagen graft (Jackson, 24 Am. J. Sports Med. 405-414 (1996)). Unlike the biomaterials and methods described herein, these methods do not allow for the preservation of the complex geometry and insertion sites of the articular cartilage, and in fact, no current surgical method of treatment has been shown to effectively reverse, ameliorate, or treat the osteoarthritis that develops after an ACL injury. The biomaterials and methods described herein, which delay and/or prevent the onset of premature osteoarthritis after an ACL injury, thus have advantages over the previous devices and methods. Moreover, no studies to date have specifically investigated the use of any of these materials to serve as a provisional scaffold and prevent arthritis development after primary repair of the anterior cruciate ligament, as provided herein.

The advantages of the biomaterials and methods described herein further include: (1) a less invasive treatment as compared with the current techniques, as the substance can be placed into the joint with and injection or small incision; (2) faster surgery (as opposed to current meniscal or cartilage repair techniques); (3) no donor site morbidity (as is seen with harvesting articular cartilage, periosteum, bone marrow or adipose tissue); (4) a quicker healing time; (5) a greater likelihood of the restoration of the normal function of the tissues (because the collagen scaffold is repopulated by the patient's own cells); and (6) restoration of the meniscal structure (as contrasted with meniscectomy) or the articular cartilage structure (as contrasted with total joint arthroplasty). Implanting a scaffold that facilitates the migration of the patient's own cells to the injured area (1) eliminates the waiting time for ex vivo cell culture; (2) takes advantage of local nutritional sources and blood supply; (3) avoids the need for a second procedure; and (4) avoids the sudden change in nutritional environment seen by cells transferred from laboratory culture into a patient (see, e.g., Ferber, 284(5413) Science 422-425 (1999); Ferber, 284 (5413) Science 423 (1999)).

Biomaterials

The biomaterials described herein, such as collagen materials and ECM scaffold, comprises a structural member, which comprises, e.g., collagen, a non-collagen extracellular matrix component, a synthetic polymer, or a combination thereof, and optionally one or more bioactive agents (e.g., calcium, platelet such as platelet-rich plasma, growth factor, cells such as white blood cell, red blood cell, or stem cell, cross-linking agent, and/or neutralizing agent). Such biomaterials can be formulated to form pharmaceutical compositions suitable for administering to a subject. In some examples, the biomaterials described herein contain only the structural member, e.g., collagen. In other examples, the biomaterials described herein comprise both the structural member and one or more biological agents as described herein. The biomaterials described in US20090254104, US20040059416, and U.S. Pat. No. 6,964,685 are also within the scope of the present disclosure.

(a) Structural Members

Referring to the drawings, one embodiment of the structural member of the biomaterials described herein is shown in FIG. 1, panel A. The structural member is preferably made of a compressible, resilient material which has some resistance to degradation by synovial fluid. The structural member can be made of either permanent or biodegradable materials.

Materials and scaffolds that make up the structural member can function either as insoluble regulators of cell function or simply as delivery vehicles of a supporting structure for cell migration or synthesis. Numerous matrices made of either natural or synthetic components have been investigated for use in ligament repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Many biological materials are available for making the structural member, including collagen, other extracellular matrix components, and various synthetic polymers. The non-collagen extracellular matrix components are well known in the art, including, but are not limited to, glycosaminoglycan (GAG), hyaluran, chondroitin, and non-collagen ECM proteins (e.g., keratin, elastin, fibronectin, entectin, and laminin).

In some embodiments, collagen-glycosaminoglycan (CG) copolymers can be used in the biomaterials described herein. Such copolymers have been used successfully in the regeneration of dermis and peripheral nerve. (Yannas et al., 86 Proc. Natl. Acad. Sci. USA 933-937, 1989; and Chamberlain, Long Term Functional And Morphological Evaluation Of Peripheral Nerves Regenerated Through Degradable Collagen Implants, Massachusetts Institute of Technology, 1998).

Porous natural polymers, fabricated as sponge-like and fibrous scaffolds, have been investigated as implants to facilitate regeneration of selected musculoskeletal tissues including ligaments.

In one example, Type I collagen (e.g., Type I soluble collagen) is used for making the biomaterials described herein. This type of collagen is the predominant component of the extracellular matrix for the human anterior cruciate ligament. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

Other types of collagens, such as Type II, III, IV, V, or X collagen, can also be used in the biomaterials described herein.

When necessary, the collagens can be solubilized (e.g., enzyme solubilized). For example, the collagen can be isolated from a source and mechanically minced and broken up in an enzyme based acid media rather than aqueous or salt solution. For instance, the collagen may be solubilized in pepsin. The step of mechanically mincing the collagen is important for homogenization to produce a material of uniform consistency that is free of aggregates and lumps.

The collagen can be either synthetic or naturally derived. Natural sources of collagen may be obtained from animal or human sources. For instance, it may be derived from rat, pig, cow, or human tissue or tissue from any other species. Tendons, ligaments, muscle, fascia, skin, cartilage, tail, or any source of collagenous tissue are useful. The collagen material is then implanted into a subject of the same or different species. In some examples, the implantation can be an autologous or autograft implantation. Alternatively the collagen may be obtained from autologous cells. For instance, the collagen may be derived from a patient's fibroblasts which have been cultured. In other examples, the implantation is xenogenic or xenograft implantation. The collagen may be isolated any time before surgery.

The structural member of the biomaterials described herein can also be synthetic matrices, e.g., those made of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus only degradable materials are preferred for work in regeneration. Degradable synthetic scaffolds can be engineered to control the rate of degradation.

In some embodiments, the structural member can be composed of foamed rubber, natural material, synthetic materials such as rubber, silicone and plastic, ground and compacted material, perforated material, or a compressible solid material. For example, the structural member can be made of (1) an injectable high molecular weight poly (propylene fumarate) copolymer that hardens quickly in the body (Peter et al., 10(3) J. Biomater. Sci. Polym. Ed. 363-73 (1999)); (2) a bioresorbable poly(propylenefumarate-co-ethylene glycol) copolymer (Suggs et al., 20(7) Biomaterials 683-90 (1999)); (3) a branched, porous polyglycolic acid polymer coated with a second polylactide-coglycolide polymer (Anseth et al., 17(2) Nature Biotechnol. 156-9 (1999)); or (4) a polyglycolic acid polymer, partially hydrolyzed with sodium hydroxide to create hydrophilic hydroxyl groups on the polymer that enable cells to attach (see, Niklason et al., 284 Science 489-493 (1999)). The latter material has been used as a scaffold for construction of bioartificial arteries in vitro.

The structural member of the biomaterials described herein can be any shape that is useful for implantation or administration (e.g., via direct injection) into a patient's joint, including a solid cylindrical member, cylindrical member having hollow cavities, a tube, a flat sheet rolled into a tube so as to define a hollow cavity, liquid, an amorphous shape which conforms to that of the tissue gap, or a gel.

The structural member can incorporate several different materials in different phases. The structural member may be made of a gel, porous or non-porous solid or liquid material (e.g., scaffold) or some combination of these. There may be a combination of several different materials, some of which may be designed to release chemicals, enzymes, hormones, cytokines, or growth factors to enhance the inductive qualities of the structural member. The structural member may be prepared from a solution, e.g. via lyophilization. Such a solution can have a specific osmolarity, preferably between 250 and 350 mOsm (e.g., 280-350 mOsm). Alternative or in addition, the solution can have a specific pH, preferably between 7.4 and 7.5. When necessary, the solution may have a protein content of greater than 10 mg/ml. Suitable solutions and methods for making the structural member of the present compositions include, but are not limited to, those described in US20090254104, which is incorporated by reference in the entirety.

(b) Biologic Agent

In addition to the structural member, the biomaterials (e.g., collagen materials or ECM scaffolds) described herein can also comprise one or more biologic agents, e.g., calcium, platelets (e.g., platelet-rich plasma), growth factors, cells such as white blood cells, red blood cells, stem cells, or cells engineered via recombinant technology for expressing a desired bioactive substance (e.g., a growth factor), cross-linking agents, neutralizing agents (e.g., sodium hydroxide or hydrochloric acid), and/or antibiotics. As shown in FIG. 1, panel B, one or more biologic agents can soak into a structural member as described herein and maintain contact between the structural member and the patient tissue to achieve the intended therapeutic purposes, e.g., promoting the migration of cells from tissue into the structural member.

Alternatively, the one or more biologic agents can be mixed with components of the structural member to form a solution, which can then be used to prepare the biomaterials described herein, e.g., via lyophilization of the solution. Such a solution may have the same osmolarity, pH, and/or protein content conditions as described above. If necessary, the solution may also comprise an anticoagulant, including, but not limited to, EDTA, acid-citrate dextrose, sodium citrate dextrose or heparin.

In some embodiments, the biologic agent is liquid containing a platelet. This can be blood or platelet-rich-plasma. Platelets can be derived from the subject to be treated. Alternatively, platelets can be derived from a donor that is allogeneic to the subject. In a non-limiting example, platelets may be isolated from a subject's blood using techniques known to those of ordinary skill in the art. As an example, a blood sample may be centrifuged at 700 rpm for 20 minutes and the platelet-rich plasma upper layer removed. Platelet density may be determined using a cell count as known to those of ordinary skill in the art. The platelet rich plasma may be mixed with collagen and used as a scaffold. The platelet rich plasma may be mixed with any one or more of the scaffold materials of the invention.

In other embodiments, the biologic agent is a growth factor. Examples include, but are not limited to platelet derived growth factor-AA (PDGP-AA), platelet derived growth factor-BE (PDGF-BB), platelet derived growth factor-AB (PDGF-AB), transforming growth factor beta (TGF-β), epidermal growth factor (EGF), acidic fibroblast growth factor (aFGF), basic fibroblast growth factor (bFGF), insulin-like growth factor-I (IGF-1), interleukin-1-alpha (IL-Ia), and insulin (see, DesRosiers et. al., 14 J. Orthop. Res. 200-9 (1996); Schmidt et al., 13 J. Orthop. Res. 184-90 (1995); Spindler et al., 14, J. Orthop. Res. 542-6 (1996)).

In some embodiments, the biomaterials described herein comprise one or more cross-linking agents to enhance the formation or attachment of the biomaterials to the tissue. The cross-linking agents can be chemicals, such as glutaraldehyde or alcohol. Alternatively, cross-linking can also be achieved by physical means, such as heat, ultraviolet (UV) light, dehydrothermal treatment, or laser treatment. Physical cross-linking methods avoid the release of toxic by-products. Dehydrothermal cross-linking is achieved through drastic dehydration which forms interchain peptide bonds. Ultraviolet irradiation is believed to form cross-links between free radicals which are formed during irradiation.

The degree to which the properties of the scaffold are affected by cross-linking is dependent upon the method and degree of cross-linking. Crosslinking with glutaraldehyde has been widely used to alter the strength and degradation rate of collagenbased biomaterials scaffolds (Kato & Silver, 11 Biomaterials 169-175 (1990), Tones, Effects Of Modulus Of Elasticity Of Collagen Sponges On Their Cell-Mediated Contraction In Vitro (Massachusetts Institute of Technology, 1998); Troxel, Delay Of Skin Wound Contraction By Porous Collagen-GAG Matrices (Massachusetts Institute of Technology, 1994)), and glutaraldehyde-cross-linked collagen products are commercially available for implant use in urologic and plastic surgery applications.

Cross-linking of collagen-based scaffolds affects the strength, biocompatibility, resorption rate, and antigenicity of these biomaterials (Torres, *Effects Of Modulus Of Elasticity Of Collagen Sponges On Their Cell-Mediated Contraction In Vitro* (Massachusetts Institute of Technology, 1998); Troxel, *Delay of skin wound contraction by porous collagen-GAG matrices* (Massachusetts Institute of Technology, 1994); Weadock et al., 29 J. Biomed. Mater. Res. 1373-1379 (1995)).

In a preferred embodiment, the biologic agent in the biomaterials described here is calcium. The calcium may be in a specific concentration such as it is sufficient to induce blood clotting when the biomaterial is co-used with a blood sample. Blood samples that are stored for medical uses often contain an anti-coagulant agent to prevent blood clotting. Many anticoagulants work by binding calcium ions, thereby preventing the coagulation proteins from using them. The calcium ions in the biomaterials described herein can counteract the effect of the anticoagulant in the blood sample, resulting in blood clotting. In some examples, the ratio of calcium to collagen can range 0.005-10 gm $CaCl_2$/gm collagen (e.g., 0-1 gm $CaCl_2$/gm collagen, 0.5-5 gm $CaCl_2$/gm collagen, 1 to 10 gm $CaCl_2$/gm collagen, 0.1 to 1 gm $CaCl_2$/gm collagen, or 0.01 to 0.1 gm $CaCl_2$/gm collagen).

In some embodiments, calcium is added to any of the solutions described herein for preparing the structural member or the biomaterial also described herein, e.g., prior to lyophilization and/or neutralization. The concentration of calcium in the solution may be between 0.001 and 100 mOsm (e.g., 10 mOsm to 100 mOsm). In some examples, the concentration of calcium in the solution is at least 90 mOsm. In some examples, the volume of a 1M calcium solution added to the structural member may range from 0.001 ml of the solution (1M) per gm of solution making the structural member to 100 ml/gm, with the preferred embodiment between 0.01 ml and 0.1 ml of calcium 1M solution per gm of solution making the structural member. Alternatively, calcium may be added after lyophilization of the solution. A second lyophilization step may be used to remove the water from the calcium solution. The concentration of calcium added to the structural member may be specific.

In one example, a composition comprising at least one ECM component such as collagen mixed with a calcium solution having a suitable concentration (e.g., around 10 mM to 250 mM, such as 30-60 mM, 30-90 mM, 30-120 mM, 60-90 mM, or 90-120 mM) to form a mixture. The mixture is then lyophilized to form a ECM sponge such as a collagen sponge. Optionally, the ECM sponge can be rehydrated to produce a gel having a high concentration of the ECM component (e.g., collagen). The ECM sponge (e.g., rehydrated) can then be neutralized (e.g., by a HEPES buffer) to produce a calcium-containing ECM scaffold.

In another example, a collagen solution can be lyophilized first and then rehydrated. The collagen slurry thus produced can be neutralized by a method known in the art (e.g., using a HEPES buffer) and then incubated under suitable conditions to allow for gelation. The collagen gel thus formed can be lyophilized to produce a collagen sponge. Afterwards, the collagen sponge can be soaked in a calcium solution having a suitable calcium concentration (e.g., those described herein) for a suitable period and then lyophilized to produce a calcium-containing collagen material. In another embodiment, the structural member and the biomaterials described herein are substantially free of thrombin. In another embodiment, no non-autologous thrombin is added to the biomaterial before, during, or after implantation. In another embodiment, thrombin from any source is added to the biomaterial before, during, or after implantation. In another embodiment, the only thrombin that is added to the biomaterial before, during, or after implantation is that found in the autologous blood or plasma comprising the implanted or injected material.

In some embodiments, the biomaterial described herein (e.g., collagen materials or ECM scaffolds) are substantially free of one or more of the following cell components: nucleic acid (DNA and/or RNA), glycosaminoglycan (GAG), phospholipid, active pepsin, and active virus. Such compositions can be prepared by treating the biomaterial, the structural member contained therein, or the solution for preparing the biomaterial/structural member to remove DNA, DNA fragments, RNA and RNA fragments, cells, fragments of cell membrane, cell components, and/or to minimizes the incorporation of endotoxins. The biomaterials, structural members, and/or solutions for preparing such can also be treated to inactivate pepsin and remove/inactivate viruses. Such treatments can be performed following methods known in the art and/or those descried herein (see Examples 7 and 8 below).

In some embodiments, the composite of structural members and biomaterials described herein (e.g., collagen materials or ECM scaffolds and/or a bio-active agent added to the collagen or ECM materials) are substantially free of one or more of the following components: thrombin, non-autologous cellular components, active pepsin, and active virus. Such compositions can be prepared by treating the biomaterial, the structural member contained therein, or the solution for preparing the biomaterial/structural member to remove thrombin, DNA, DNA fragments, RNA and RNA fragments, cells, fragments of cell membrane, cell components, and/or to minimizes the incorporation of endotoxins or viruses. The biomaterials, structural members, and/or solutions for preparing such can also be treated to inactivate pepsin and remove/inactivate viruses. Such treatments can be performed following methods known in the art and/or those descried herein (see Examples 7 and 8 below).

For example, methods for removing cell components can involve the use of detergents, including SDS, EDTA, TritonX, polyethylene glyco, citrate, and sodium deoxycholate.

These methods may also include the use of a surfactant. In addition, these methods may involve the use of enzymes, including trypsin, collagenase, elastase, DNAse and RNAse, ribonuclease, deoxyribonuclease, alpha-galactosidase, and other enzymes which can degrade cell membranes, receptors, or other cellular components. These methods may also include physical processes, including ultrasound, electron beam irradiation and gamma irradiation.

For each of these solutions containing one or more agents noted above, concentrations of solutions from 0.001% to 50% may be used. Preferred embodiments are for solutions in the range of 0.001 to 1.0%. Other preferred embodiments are for solutions in the range of 0.1 to 10.0%. Other solutions may be used in concentrations of IU/ml, for example, DNAse may be used in a concentration of 150 IU/ml.

In some examples, the pepsin in a biomaterial as described herein can be inactivated by bringing the pH of an ECM slurry such as a collagen slurry above 4.0 using a strong base such as NaOH or LiOH or KOH. Other bases include $Ba(OH)_2$ and $Sr(OH)_2$ can also be used to increase the pH of the solution and inactivate the pepsin. To inactivate the pepsin, a suitable volume of a suitable concentration of the strong base is added dropwise to the pepsin-containing slurry and the pH is recorded. This process is repeated until the pH of the slurry is above 4.0. Alternatively, the exact amount of the strong base that needs to be added is calculated based on the hydrogen ion content in the volume of slurry that needs to be counteracted by the strong base to raise the pH of the solution significantly and then that exact volume is measured and the pH is checked to ensure it is above 4.0. In other embodiments, the process is done in either of these two ways, but additional strong base is added until the pH reaches 6.0. In other embodiments, the process is done in either of these two ways, but additional strong base is added until the pH reaches 7.0 or greater. In other embodiments, the process is done in either of these two ways, but additional strong base is added until the pH reaches 8.0 or greater. In other embodiments, the process is done in either of these two ways, but additional strong base is added until the pH reaches 9.0 or greater. In other embodiments, the process is done in either of these two ways, but additional strong base is added until the pH reaches 10.0 or greater. In other embodiments, the process is done in either of these two ways, but additional strong base is added until the pH reaches 11.0 or greater. In other embodiments, the process is done in either of these two ways, but additional strong base is added until the pH reaches 5.0 or greater.

Once the slurry reaches its target pH range, the solution is kept there for a specific amount of time. This time may be between 10 seconds and 1 week. In a preferred embodiment, the time is between 1 and 10 minutes. In another preferred embodiment, the time is between 10 and 30 minutes. In another preferred embodiment, the time is between 10 and 60 minutes.

After inactivation of the pepsin, the pH of the slurry is returned to a pH between 7.0 and 8.0 by the addition of a buffer with a pK of between 7 and 8, such as a buffer containing TAPSO, HEPES, TES, MOPS, Cacodylate SSC or Succinic acid. Alternatively, phosphate buffered saline may be used, or $K_2HPO_4$. Any combination of a weak acid and its conjugate base, or a weak base and its conjugate acid may be used. A buffer of carbonic acid and bicarbonate may also be used. Blood or plasma containing carbonic acid and bicarbonate may be used. A universal buffer, such as that using citric acid and Na2HPO4 (McIlvaine's buffer solutions) may also be used in proportions that yield a buffer range of pH between 7 and 8.

Upon treatment as described above, the biomaterial described herein is substantial free of one or more of nucleic acid (DNA and/or RNA), glycosaminoglycan (GAG), phospholipid, active pepsin, and active virus. In some examples, the nucleic acid and/or phospholipid content in the biomaterial (e.g., dry weight) described herein is less than 20% of that in a native tissue such as dermis (e.g., less than 15%, 10%, 5%, or 1%). In other examples, the content of GAG in the biomaterial is less than 50% (e.g., 40%, 30%, 20%, 15%, 10%, or 5%) of the total dry weight of the biomaterial. In other examples, the level of active pepsin in the biomaterial described herein is less than 1000 ug/ml, e.g., less than 500 ug/ml, 200 ug/ml, or 100 ug/ml.

In some examples, viruses can be inactivated by ethylene oxide sterilization, e-beam sterilization, or gamma irradiation.

When necessary, the biomaterials described herein (e.g., collagen materials) can contain GAG. In some examples, the content of GAG in the biomaterials can be at least 20% of the total dry weight of the material. For example, the biomaterials can contain 20-50%, 20-30%, 20-40%, or 20-50% GAG by weight.

Medical Uses of Biomaterials

The biomaterials described herein, including collagen materials such as collagen gels and collagen sponges, and ECM scaffolds, can be used to prevent and/or minimize progression of injuries to the anterior cruciate ligament, the meniscus, labrum, cartilage, and other tissues exposed to synovial fluid after injury. They also can be used to alleviate and/or reduce the risk for developing arthritis (e.g., osteoarthritis), such as post-traumatic arthritis.

In some embodiments, the biomaterials described herein (e.g., the ECM scaffolds such as collagen scaffolds) are designed for use in an arthroscopic surgery with arthroscopic equipment. The scaffold can be compressible to allow introduction through arthroscopic portals and equipment. When desired, the scaffold can also be pre-treated in antibiotic solution or sterilization via a routine method prior to implantation. When a collagen-based scaffold is used in the treatment described herein, the affected extremity is prepared and draped in the standard sterile fashion. A tourniquet may be used if indicated. Standard arthroscopy equipment may be used. After diagnostic arthroscopy is performed, and an intra-articular lesion identified and defined, tissues desired for protection are pretreated, either mechanically or chemically, and the scaffold introduced into the joint. The scaffold is then bonded to the surrounding tissue by creating chemical or mechanical bonds between the tissue proteins and the scaffold biologic agent. This can be done by the addition of a chemical agent or a physical agent such ultraviolet light, a laser, or heat, the scaffold may be reinforced by placement of sutures or clips. The arthroscopic portals can be closed and a sterile dressing placed. The post-operative rehabilitation is dependent on the joint affected, the type and size of lesion treated, and the tissue involved.

Figure 2:
FIG. 2 is a schematic illustration of an embodiment of the biomaterial described herein for coating an articular cartilage. Panel A depicts an exemplary biomaterial coating an articular cartilage. Panel B depicts the biomaterial linked to the cartilage surface. Panel C depicts cells migrating into the exemplary biomaterial, reinforcing and thickening the articular cartilage.
Figure 2:
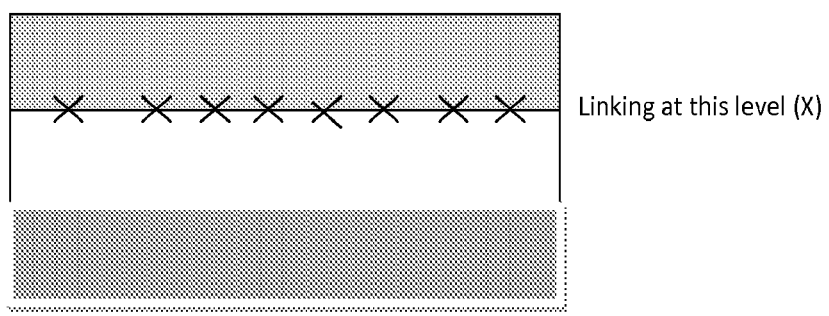
Figure 2:
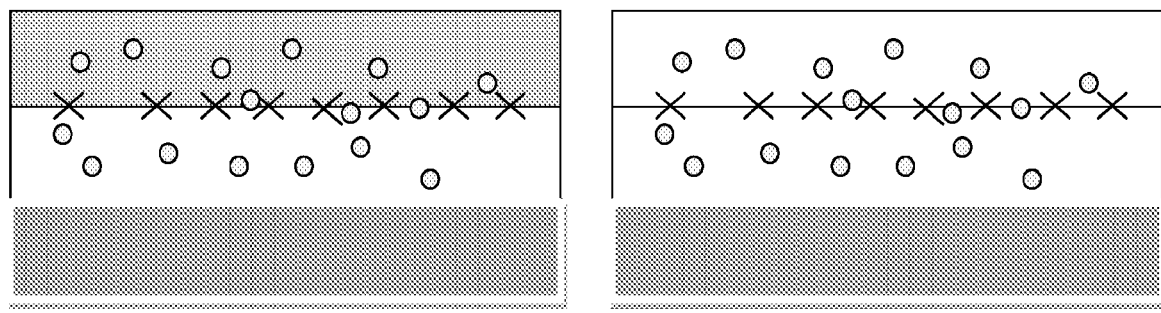
Figure 3:
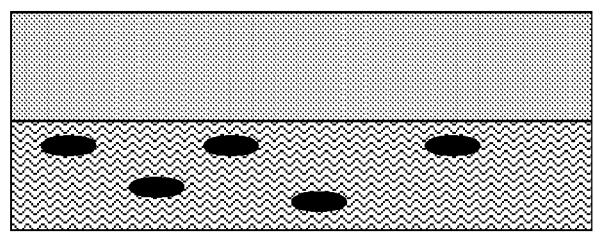
FIG. 3 is a schematic illustration of an embodiment of the biomaterials described herein for coating a ligament or tendon. Panel A depicts an exemplary biomaterials coating a ligament or tendon. Panel B depicts the exemplary biomaterial linking to the ligament or tendon surface. Panel C depicts cells migrating into the exemplary biomaterials, reinforcing and thickening the ligament or tendon.
Figure 3:
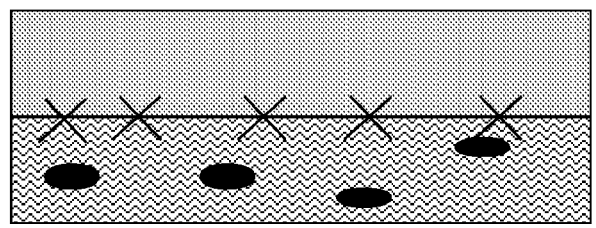
Figure 3:
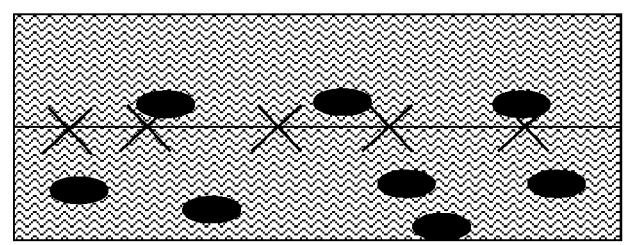
Figure 4:
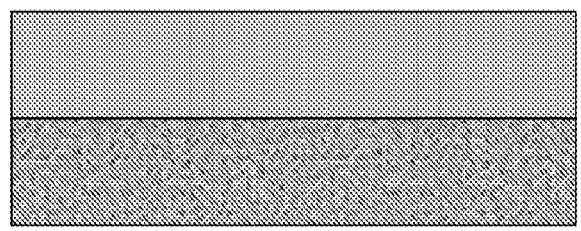
FIG. 4 is a schematic of an embodiment of the biomaterials described herein for coating a meniscus. Panel A depicts an exemplary biomaterial coating a meniscal surface. Panel B depicts the exemplary biomaterial linking to the meniscal surface. Panel C depicts cells migrating into the exemplary biomaterial, reinforcing and thickening the meniscus.
Figure 4:
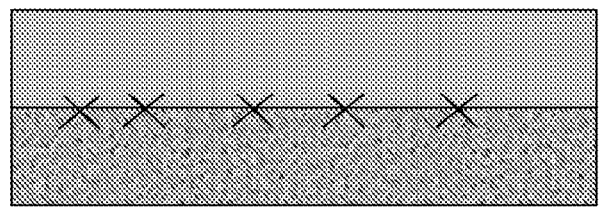
Figure 4:
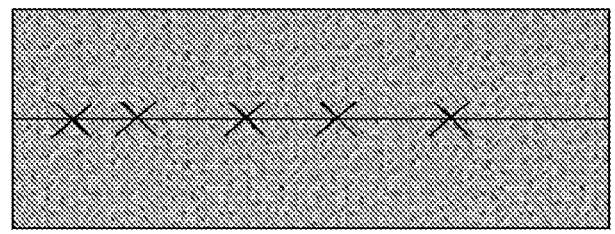

In an arthroscopic surgery, the contact between the scaffold and the surrounding tissue can be accomplished by formation of chemical bonds between the material of the core and the tissue, or by bonding the material of the core to the biologic agent combined with bonding the biologic agent to the surrounding tissue. Mechanical bonds can be formed that interlock the core with the tissue. Alternatively, pressure can be maintained on the core/tissue interface. FIGS. 2-4. For example, the biomaterial as described herein can be placed to coat a surface of a tissue where repair is needed, e.g., cartilage, ligament, tendon, or meniscus. The biomaterial is then linked to the tissue, allowing migration of cells in the tissue into the biomaterial and reinforcing/thickening the tissue to be repaired.

In other embodiments, an effective amount of the biomaterial described herein (e.g., collagen gels) can be administered to a joint of a subject where treatment is needed via, e.g., direct injection. The subject matter may have or may be at risk for developing arthritis (e.g., osteoarthritis) at the joint. In some embodiments, the subject has an intra-articular injury at the joint, e.g., an acute joint injury. An intra-articular injury can be any type of injury (e.g., rupture) to any tissue of a joint, including, but not limited to, ligament, cartilage, tendon, and meniscus. The subject treated by the collagen material may not be concurrently surgically treated to repair a torn or ruptured intra-articular tissue. In some examples, the subject was surgically treated for a torn or ruptured intra-articular tissue at the joint at least one day (e.g., at least 3 days, 5 days, one week, two weeks, or one month) prior to the administration of the collagen material.

In one example, the collagen material is administered to the joint of a subject in an amount effective in alleviating or reducing the risk for developing arthritis associated with joint injury or joint surgery. Such an effective amount will depend, of course, on the particular condition being treated, the severity of the condition, the individual subject's parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The details of one or more embodiments of the invention have been set forth in the accompanying description above. Although any methods and materials similar or equivalent to those described herein can be used in the practice or testing of the present invention, the preferred methods and materials have been described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs.

The following EXAMPLES are presented to more fully illustrate the preferred embodiments of the invention. These EXAMPLES should in no way be construed as limiting the scope of the invention, as defined only by the appended claims.

Example 1

Outgrowth of Chondrocytes from Human Articular Cartilage Explants and Expression of Alpha-Smooth Muscle Actin The objectives of this EXAMPLE were to investigate the effects of enzymatic treatment on the potential for cell outgrowth from adult human articular cartilage and to determine if $\alpha$-smooth muscle ($\alpha$-sm) is present in chondrocytes in articular cartilage and in the outgrowing cells.

Material and Methods

Samples of articular cartilage were obtained from 15 patients undergoing total joint arthroplasty for osteoarthrosis. While the specimens were obtained from patients with joint pathology, areas of cartilage with no grossly noticeable thinning, fissuring, or fibrillation were selected. Using a dermal punch, cylindrincal samples (4.5 mm diameter and 2-3 mm thick), were cut from the specimens. Explants were cultured in 6-well culture dishes and oriented so that deep zone of the tissue contracted the culture dish. In the first test, 20 cartilage samples were obtained from each of the 9 patients. Four plugs of cartilage were allocated to one of five groups that received collagenase treatment for 0, 1, 5, 10, or 15 min. The time to cell attachment after outgrowth was determined and cultures were terminated after 28 days. From 6 of the 9 patients, additional plugs, untreated and treated with collagenase for 15 minutes, were evaluated for $\alpha$-sm, immediately after treatment, and at 6, 14 and 20 days in culture. In the second test, 24 cartilage plugs were obtained from each of 6 additional patients. Four plugs were allocated to 5 groups receiving a different enzymatic treatment for 15 min. and a sixth untreated control group: (a) 380 U/ml clostridial collagenase (0.1%; Sigma Chemical, St. Louis, Mo.); (b) 1100 U/ml hyaluronidase (0.1%; Sigma Chemical); (c) 1 U/ml chondroitinase ABC (Sigma Chemical), (d) 0.05% trypsin (Life Technologies); and (e) 1100 U/ml hyaluronidase followed by 380 U/ml collagenase (7.5 min. in each). The days when cell outgrowth (round cells separated from the explant) and cell attachment (elongated cells) were first evident were recorded. All cultures were terminated after 30 days. If no outgrowth was noted, time to outgrowth was assigned 28 or 30 days for experiment 1 and experiment 2, respectively.

Explants allocated for immunohistochemistry were fixed in 10% formalin, paraffin embedded and cut to 7-11 m sections. Sections were stained with a a-sm monoclonal antibody (Sigma Chemical, St. Louis, Mo.). Statistical analysis was performed by ANOVA with Fisher's PLSD post-hoc test.

Results

The time to cell attachment after outgrowth from untreated explants was >4 weeks with no sign of outgrowth in 6 of 9 explants. There was a significant effect of collagenase treatment time on the time to cell attachment ($p<0.001$).

TABLE 1

Times to cell attachment after collangenase treatments of cartilage explants (Mean ± SEM: n = 9)

| Explant Treatment | Days |
| --- | --- |
| Untreated | 27.2 ± 0.4 |
| 1-min collangenase | 15.4 ± 2.6 |
| 5-min collangenase | 9.9 ± 1.0 |
| 10-min collangenase | 6.2 ± 0.4 |
| 15-min collangenase | 5.9 ± 0.4 |

Treatments with hyaluronidase, chondroitinase ABC, and trypsin had no effect on the times to outgrowth and attachment (TABLE 2). In contract, the collagenase treatment yielded a time to outgrowth of at least 1 order of magnitude less than the untreated group (2.2±0.2 vs 27.7±1.5 days, respectively; TABLE 2). Treatment of the explants with hyaluronidase +collagenase yielded results that were comparable to treatment with collagenase alone. Signs of attachment of the outgrowth cells were generally found within 3 days of the first evidence of outgrowth.

TABLE 2

Times to outgrowth and attachment of chondrocytes from articular cartilage explants after various enzymatic treatments (Mean ± SEM; n = 6)

| Group | Time to Outgrowth (days) | Time to Attachment (days) |
|---|---|---|
| Untreated | 27.7 ± 1.5 | 28.5 ± 1.0 |
| Collagenase | 2.2 ± 0.2 | 5.8 ± 0.6 |
| Hyaluronidase | 25.0 ± 1.6 | 27.5 ± 0.9 |
| Chondroitinase ABC | 29.2 ± 0.8 | 29.7 ± 0.3 |
| Trypsin | 28.8 ± 1.2 | 29.5 ± 0.5 |
| Hyaluronidase + Collagenase | 2.5 ± 0.3 | 5.0 ± 0.4 |

Immunohistochemistry revealed that approximately 70% of the chondrocytes in the explants stained positive for the a-sm isoform (TABLE 3). The chromogen was restricted to the cytoplasm of the cells that displayed the typical chondrocyte morphology and location in lacunae. There was no significant difference in the percentage of a-sm-staining cells in the explants in the collagenase and untreated control groups, at any time period in culture (TABLE 3). There were significant increases in the percentage of a-sm-containing cells in the untreated and collagenase-treated groups after 14 days in culture, compared to the initial values (TABLE 3; $p<0.02$ and $p<0.01$, respectively). After 20 days, there was a decrease in the number of cells in all explants and a significant reduction ($p<0.001$) in the % of a-sm-containing cells in the explants, compared to 14 days (TABLE 3). The percentage of attached cells from all groups that stained positive for a-sm was greater than 90%.

TABLE 3

The percentage of cells in untreated and collangenase-treated articular cartilage explants containing α-smooth muscle actin, after various time in culture (Mean ± SEM.; n = 6)

| Groups | Initial | 6 days | 14 days | 20 days |
|---|---|---|---|---|
| Untreated | 68 ± 9 | 78 ± 7 | 92 ± 5 | 49 ± 11 |
| 15-min collagenase | 74 ± 8 | 93 ± 2 | 98 ± 2 | 51 ± 5 |

Discussion

The notable findings of this EXAMPLE were that the rate of chondrocyte outgrowth from adult human articular cartilage could be profoundly accelerated by collagenase treatment and that chondrocytes in adult human osteoarthritic articular cartilage contain a contractile actin isoform not previously identified in this cell type. The investigation of cartilage from joints with arthritis is useful, as this is the population that may benefit from facilitated cartilage repair. The results of this EXAMPLE show that collagen architecture limits chondrocyte migration. Thus, this Example shows that, if migration of chondrocytes to a wound edge in vitro can be facilitated, the cells contribute to the healing process by contracting an endogenous or exogenous scaffold bridging the defect.

Example 2

The Migration of Cells from the Ruptured Human Anterior Cruciate Ligament into Collagen-Based Regeneration Templates Introduction One object of the present disclosure is to restore only the ligament tissue which is damaged during rupture, while retaining the rest of the ligament. The model used in this EXAMPLE involves filling the gap between the ruptured ligament ends with a bioengineered regeneration bridge, or template, designed to facilitate cell ingrowth and guided tissue regeneration. In this EXAMPLE, one of the critical steps in guided tissue regeneration was investigated, namely, the ability of cells in the adjacent injured ligament tissue to migrate into the regeneration template. This EXAMPLE focuses on whether the cells of the human anterior cruciate ligament cells are able to migrate to a template after the anterior cruciate ligament has been ruptured. It was also intended to show that the cells which migrated expressed a contractile actin isoform, α-sm actin, which may contribute to contraction of the template and self-tensioning of the ligament.

Methods

Four ruptured anterior cruciate ligaments were obtained from 4 men undergoing anterior cruciate ligament reconstruction, ages 25 to 34, with an average age of 28 years. Time between injury and ligament retrieval ranged from 6 to 20 weeks. Synovial tissue covering the ligaments was removed and the ligament remnants cut lengthwise into two sections. One longitudinal section from each ligament (n=4) was allocated for histology. The remaining section was transected into thirds along its length. Each section was divided into 5 biopsies, or explants, four of which were placed into culture with the collagen-glycosaminoglycan regeneration template, and one of which was placed onto a petri dish for 2-D explant culture. The site closest to the rupture, or injury zone, contains a higher cell number density than that of the more distal remnant, which resembles the histology of the intact anterior cruciate ligament. Therefore, the more distal remnant (normal zone) was used as an age and gender matched control for the tissue obtained at the site of injury (injury zone) and 0.5 cm distal to the site of injury (middle zone).

Results

Explant Culture on a 2-D Surface.

The 12 tissue biopsies from the three sections of the four ligaments were explanted onto tissue-culture treated 35 mm wells (Corning #430343, 6 well plates, Cambridge, Mass.) and cultured in 1 cc of media containing Dulbecco's DMEMI F12 with 10% fetal bovine serum, 2% penicillin streptomycin, 1% amphotericin B, 1% L-glutamine and 2% ascorbic acid. Media was changed 3× a week. Outgrowth from the explant biopsies was recorded every three days as the surface area covered by confluent fibroblasts. The area of outgrowth was measured using an inverted microscope and a transparent grid sheet. The number of squares covered by the confluent cells was counted and the area calculated by multiplying the number by the known area of each square. The effective radius of outgrowth was calculated by dividing the total area of confluent cells by 1 t (3.14) and taking the square root of the result. The rate of outgrowth was then calculated by plotting the average effective radius of outgrowth as a function of time since confluent outgrowth was first observed and calculating the slope of the linear relationship. Seven zones were not found to be statistically significant (p=0.66). Two-way ANOVA demonstrated the effect of explant location in the ligament had a significant effect on cell number density, but that time in culture did not have a significant effect. Cells migrating into the collagen-glycosaminoglycan scaffold demonstrated all of the three previously described ligament fibroblast morphologies: fusiform or spindle-shaped, ovoid, and spheroid.

The maximum cell number density in the template at the four week time period was found to directly correlate with cell number density of the explant tissue ($r^2$=0.24), to inversely correlate with density of blood vessels in the explant tissue ($r^2$=0.28), and not to correlate with the percentage of a-sm actin positive cells in the explant tissue ($r^2$=0.00). All cells which migrated into the C template were found to be positive for a-sm actin at the 1 and 2 week period.

Template Contraction.

The templates were noted to decrease in size during the four weeks of culture. Those templates cultured without tissue contracted an average of 19.0%+0.7%. Templates cultured with tissue contracted between 17 and 96%. A greater maximum cell number density of a-sm actin positive cells within the template was found to correlate with a greater rate of scaffold contraction (r2=0.74).

The 3-D culture substrate used in this EXAMPLE was a highly porous collagen-glycosaminoglycan matrix, composed of type I bovine hide collagen and chondroitin-6-sulfate, prepared by freeze-drying the collagen-glycosaminoglycan dispersion under specific freezing conditions (Yannas et al., 8 Trans Soc Biomater. 146 (1985)) to form a tube with pore orientation preferentially oriented, longitudinally. The average pore size of the collagen-glycosaminoglycan scaffold manufactured in this manner has previously been reported as 100 gm (Chamberlain, *Long Term Functional And Morphological Evaluation Of Peripheral Nerves Regenerated Through Degradable Collagen Implants.* (Massachusetts Institute of Technology, 1998)).

Immunohistochemistry.

The expression of a-sm actin was determined using monoclonal antibodies. For the 3-D culture specimens, deparaffinized, hydrated slides were digested with 0.1% trypsin (Sigma Chemical, St. Louis, Mo., USA) for 20 minutes. Endogenous peroxide was quenched with 3% hydrogen peroxide for 5 minutes. Nonspecific sites were blocked using 20% goat serum for 30 minutes. The sections were then incubated with mouse anti-a-sm actin monoclonal antibody (Sigma Chemical, St. Louis, Mo., USA) for one hour at room temperature. Negative controls were incubated with mouse serum diluted to an identical protein content. The sections were then incubated with biotinylated goat anti-mouse IgG secondary antibody for 30 minutes followed by thirty minutes of incubation with affinity purified avidin. The labeling was developed using the AEC chromagen kit (Sigma Chemical, St. Louis, Mo.) for ten minutes. Counterstaining with Mayer's hematoxylin for 20 minutes was followed by a 20 minute tap water wash and coverslipping with warmed glycerol gelatin.

Histology of the Ligament Fascicles.

The proximal one-third was populated predominantly by fusiform and ovoid cells in relatively high density, and the distal two-thirds was populated by a lower density of spheroid cells. The levels of transection used to obtain the biopsies were resulted in an injury zone which contained an average cell number density of 2083+982 cells/mm$^2$ (n=4), a middle zone with an average cell number density of 973+397 cells/mm$^2$ (n=4), and a normal zone with an average cell density of 803+507 cells/mm$^2$ (n=4). The cell number density in the injury zone was higher in the specimen obtained twenty weeks after injury (4318 cells/mm$^2$, n=1) when compared with the remnants obtained six weeks (394 cells/mm$^2$, n=1) and eight weeks after injury (1811 cells/mm$^2$, n=2). a-sm actin immunohistochemistry of the ruptured ligaments showed positive staining in 2 to 20% of fibroblasts not associated with blood vessels.

2-D Culture Outgrowth.

The outgrowth of cells onto the 2-D culture dishes was observed to occur as early as 3 days and as late as 21 days, with outgrowth first detected at an average of 6.6±2.0 days after explanting. Explant size was not found to correlate with the time of onset or rate of outgrowth. Linear regression analysis of the plot of effective outgrowth radius versus time for all explants that demonstrated confluent outgrowth had a coefficient of determination of 0.98. The average rate of outgrowth, represented by the slope of this plot, was 0.25 mm/day.

3-D Culture Outgrowth.

In the constructs with interposed collagen-glycosaminoglycan scaffolding, fibroblasts migrated from the human anterior cruciate ligament explants into the templates at the earliest time point (1 week). At one week, migration into the templates was seen in 4 of 4 of the templates cultured with explants from the injury zone, I of 4 templates cultured with explants from the middle zone, and 1 of 4 of the templates cultured with explants from the normal zone. By four weeks, cells were seen in 3 of 3 templates cultured with the injury zone explants (the fourth template had been completely degraded) and in 3 of four of the templates cultured with the normal zone explants. Five of the explants completely degraded the template prior to the collection time. The location from which the explants were taken (injury, middle or normal) was found to have a statistically significant effect on the cell number density in the template (two-way ANOVA, p=0.001), with Bonferroni-Dunn post-hoc testing demonstrating differences between templates cultured with explants from the injury zone and middle zone (p=0.009) and the injury and normal zone (p=0.003). The difference between the template cell density for templates cultured with explants from the middle and tibial of the twelve explants (three from the injury zone, two from the middle zone, and two from the normal zone) demonstrated confluent growth for at least two consecutive time periods prior to termination and were included in the calculation of the average rate. All explanted tissue and fibroblasts on the culture wells were fixed in formalin after four weeks in culture.

Fascicular-Collagen-Glycosaminoglycan Template Constructs.

One fascicle from each of the 4 patients was divided into explants for use in the test (injury zone or middle zone and template) and control (normal zone and template) groups. This yielded two test and one control construct per patient for examination after 1, 2, 3, and 4 weeks in culture, providing eight test and four control constructs at each of the four time points.

The forty-eight constructs were made by placing the ligament explant onto a 9 mm disc of collagen-glycosaminoglycan (CG) template. All of the constructs were cultured in media containing Dulbecco's DMEMI F12 with 10% fetal bovine serum, 2% penicillin streptomycin, 1% amphotericin B, 1% L-glutamine and 2% ascorbic acid. Media was changed 3× a week. The diameter of the template was measured at each media change. Six templates without explants were cultured simultaneously and measured at each time change as controls.

One construct from the injury, middle and normal zones from each patient (n=4) were fixed and histologically examined after 1, 2, 3 and 4 weeks in culture. Two of the constructs at three weeks showed signs of low-grade infection and were excluded from the EXAMPLE. Hematoxylin and eosin staining and immunohistochemical staining for a-sm actin were performed for each construct. Sections were examined using a Vanox-T AH-2 microscope (Olympus, Tokyo, Japan) with normal and polarized light. For each template, areas of 0.1 $mm^2$ (250 by 400 micrometers) were counted, and the highest cell number within that area recorded as the maximum cell number density. This value was multiplied by 10 to obtain the number of cells per square millimeter. The fascicular tissue and collagen-glycosaminoglycan scaffolding were examined using polarized light to determine the degree of crimp and collagen alignment.

This EXAMPLE demonstrated that the cells intrinsic to the ruptured human anterior cruciate ligament were able to migrate into an adjacent regeneration template, eventually attaining small areas with cell number densities similar to that seen in the human anterior cruciate ligament in vivo. Explants from the transected region demonstrated outgrowth onto a 2-D surface with a linear increase in outgrowth radius as a function of time in culture. Cells which migrated into the collagen-glycosaminoglycan scaffold differed significantly from the populations of the ruptured anterior cruciate ligament in that while an average of 2 to 20% of cells are positive for a-sm actin in the ruptured anterior cruciate ligament, 100% of cells noted to migrate at the early time periods were positive for this actin isoform.

The investigation in this EXAMPLE implemented an in vitro model that allows for the investigation of the migration of cells directly from an explant into a 3-D collagen-glycosaminoglycan scaffold. Cells with all three previously described ligament fibroblast morphologies—fusiform, ovoid and spheroid—were noted to migrate into the scaffold. Location in the ligament from which the explant was obtained was found to significantly affect the cell number density in the template, with higher number densities of cells found to migrate from the injury zone of the ligament. These findings suggest that cells intrinsic to the human anterior cruciate ligament are capable of migrating from their native extracellular matrix onto an adjacent collagen-glycosaminoglycan scaffold, and that the zone of injury contains cells in which are capable of populating a regeneration template in greater numbers than the middle and normal zones of the ruptured ligament.

This EXAMPLE shows the potential of cells from the ruptured human anterior cruciate ligament fibroblasts to migrate into collagen-glycosaminoglycan templates that may ultimately be used to facilitate regeneration anterior cruciate ligament after even a minor injury. The model used here allows for the analysis of the migration of fibroblasts out of human tissues directly onto a porous 3-D scaffold in a controlled, in vitro, environment. This construct obviates several possible confounding factors, such as modulation of cell phenotype, which may occur during cell extraction or 2-D cell culture.

Example 3

Effects of Growth Factors and Collagen-Based Substrates the Fibroinductive Properties of Fibroblast Migration The purpose of this EXAMPLE is to determine the process of fibroblast-mediated connective tissue healing and how specific alterations in the extracellular environment alter this process. The effects of 4 different growth factors and 4 collagen based substrates on features associated with the repair processes in connective tissues which successfully heal were quantified. These processes are the fibroinductive properties of fibroblast migration, proliferation, and type I, type II, and type III collagen synthesis. The effects of environmental modifications on the expression of a contractile actin isoform, α-smooth muscle actin (α-sm) were also defined.

In EXAMPLE 3, it was demonstrated that fibroblasts in the ruptured anterior cruciate ligament are able to migrate from their native extracellular matrix into a 3-D CG scaffold in vitro. This EXAMPLE provides improved rates of migration, proliferation, and type I collagen synthesis of anterior cruciate ligament fibroblasts by altering the degree and type of cross-linking of the scaffold and by adding four different growth factors to the scaffold. The specific aims for this EXAMPLE are (1) to determine the effect of cross-linking of a collagen-based scaffold on (a) the rate of fibroblast migration, (b) the rate of fibroblast proliferation, (c) expression of a contractile actin, and (d) the rate of type I collagen synthesis by fibroblasts in the collagen-based scaffold, and (2) to determine the effect of addition of selected growth factors on these same outcome variables. Thus, this EXAMPLE determines how specific alterations in scaffold cross-linking and the addition of specific growth factors alter the fibroinductive properties of a collagen based scaffold. In this EXAMPLE, the fibroinductive potential of the scaffold is defined as its ability to promote fibroblast infiltration, proliferation and type I collagen synthesis.

Without being bound by theory, the specific aims listed above may be achieved through the following:

(1) The method and degree of cross-linking alter the rate of fibroblast migration from an anterior cruciate ligament explant into a collagen-based scaffold as well as the rate of fibroblast proliferation, expression of a contractile actin, and type I collagen synthesis within the scaffold. This is based on the results provided in the EXAMPLES above, which demonstrated that alteration in fibroblast proliferation rates and expression of the contractile actin isoform after fibroblast seeding of cross-linked scaffolds, as well as the differences in rates of collagen synthesis by chondrocytes seeded into type I and type II collagen based scaffolds. One possible mechanism for this observation is that the solubilized fragments of collagen resulting from the degradation of the collagen-based scaffold could affect cell metabolism. These fragments may form at different rates for different cross-linking methods. Validation of this mechanism demonstrates that the fibroinductive properties of the collagen-based scaffold can be regulated by the choice of cross-linking method.

In this EXAMPLE, constructs of human anterior cruciate ligament explants and crosslinked collagen-based scaffolds are used to determine the rates of cell migration, proliferation, expression of a contractile actin and type I collagen synthesis. Scaffolds cross-linked with glutaraldehyde, ethanol, ultraviolet light and dehydrothermal treatment are used. The cross-linking method correlates with the regulation of the fibroinductive properties of the scaffold.

(2) The addition of growth factors to the CG scaffold alters the rates of fibroblast migration from an anterior cruciate ligament explant to a collagen-based scaffold as well as the rates of fibroblast proliferation, expression of a contractile actin, and type I collagen synthesis within the scaffold. The rationale for this hypothesis is the alteration in fibroblast migration rates onto 2-D surfaces and synthesis of type I collagen in vitro when growth factors are added to the culture media, as well as alteration in rates of incisional wound healing with the addition of growth factors. Validation of this hypothesis shows how the fibroinductive properties of the collagen-based scaffold may be regulated by the addition of a specific growth factor. The growth factors to be studied in this EXAMPLE include TGF-β, EGF, bFGF and PDGF-AB. Constructs of human anterior cruciate ligament explants and collagen-based scaffolds cultured in media containing growth factors are used to determine the rates of cell migration, proliferation, expression of a contractile actin and type I collagen synthesis in these constructs. The control wells contain only 0.5% fetal bovine serum, a protocol which has been reported previously by DesRosiers et al., 14 J. Orthop. Res. 200-208 (1996). Presence of the growth factors was found to correlate with the regulation of the fibroinductive properties of the scaffold. See also Murray et al., J. Orthopaedic Research 21 (2003) 238:244.

Assay Design.

The assay design is similar to that of EXAMPLE 4. Human anterior cruciate ligament explants are obtained from patients undergoing total knee arthroplasty. Ligaments which are grossly disrupted or demonstrate gross signs of fatty degeneration are excluded from the analysis. A fairly uniform distribution of cells occurs in the distal ⅔ of the ligament fascicles, so this section is used for all assays. The preparation of the collagen-based scaffold is as described in EXAMPLE 4 and previously reported by Torres, Effects Of Modulus Of Elasticity Of Collagen Sponges On Their Cell-Mediated Contraction In Vitro (Massachusetts Institute of Technology, 1998). The cross-linking of the scaffolds is as described in EXAMPLE 4 and as previously described by Tones, Effects Of Modulus Of Elasticity Of Collagen Sponges On Their Cell-Mediated Contraction In Vitro (Massachusetts Institute of Technology, 1998). The growth factors are added to the cell culture media as described in EXAMPLE 4. Culture, histology for analysis of cell migration, DNA assay for cell proliferation, immunohistochemistry for the contractile actin isoform, and SDS-PAGE analysis for the synthesis of type I collagen are as described in EXAMPLE 4. A pilot assay is performed to assess the DNA content with the DHT cross-linked scaffold with the addition of no growth factors. Alternatively, a tritiated thymidine assay can be evaluated or the specimens used for proliferation can be fixed and serially sectioned, with sections at regular intervals examined for cell number density. Maximum number density is recorded for each specimen type. Associated histology is used to estimate the percentage of dead cells.

Example 4

Treatment of Partial ACL Tears in Vivo

To test whether treating a partial ACL tear with a collagen-PRP scaffold enhances healing of the ACL and prevents progression of the tear, partial ACL defects were treated with collagen PRP scaffolds and the histologic and biomechanical responses for treated ACLs compared with untreated control ACLs.

Materials and Methods

Two experiments were performed in this study. In the first experiment, bilateral partial ACL injuries were made and one side treated with the collagen-PRP hydrogel. A histologic comparison of treated and untreated ligaments for each animal was performed at 3 (n=5) and 6 (n=5) weeks. In the second experiment, unilateral partial ACL injuries were treated with the collagen-PRP scaffold and the biomechanical properties of the treated ligaments measured at six weeks (n=8). The tensile properties of the healing ligament were normalized by the intact contralateral ACL for each animal. These normalized results (Tx-6) were compared with identically obtained normalized results for two previously reported control groups—a normalized untreated defect at zero weeks (UnTX-0) and a normalized untreated defect at six weeks (UnTx-6).

Results

Figure 5:
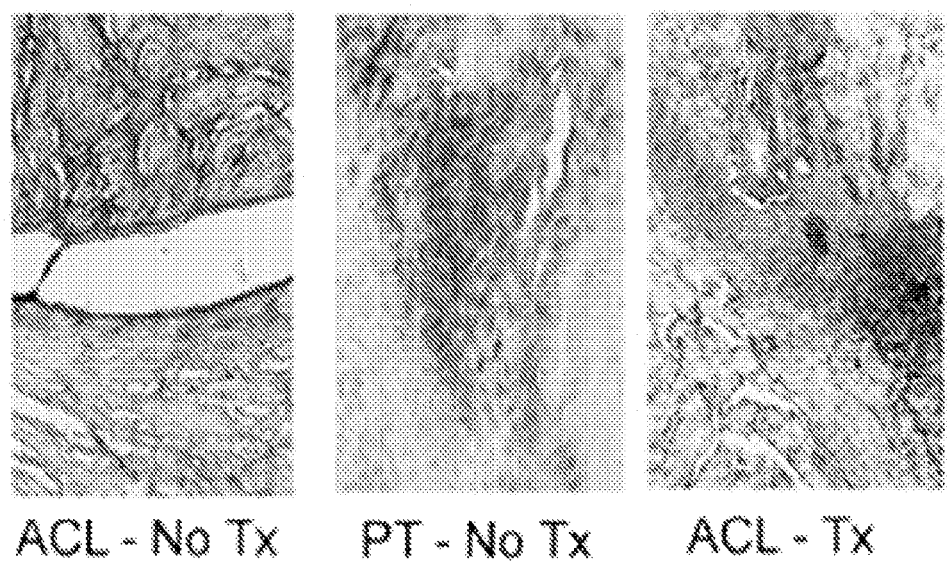
FIG. 5 depicts immunohistochemistry for fibrinogen in an untreated ACL defect (left). Note persistent white gap between ligament edges even after six weeks in vivo. In center, the defect in the patellar tendon has filled with a fibirinogen positive tissue. On the right, addition of a collagen-PRP scaffold to the ACL defect has resulted in formation of a fibirinogen positive material forming in the ACL defect in vivo.

Histology:

The percentage filling of the defects in the treated ACLs was significantly higher at both the three and six week time points compared with the untreated controls (50±21% vs. 2±2% at three weeks, and 43±11% vs. 23±11 at six weeks, values=mean±SEM; FIG. 5).

Figure 6:
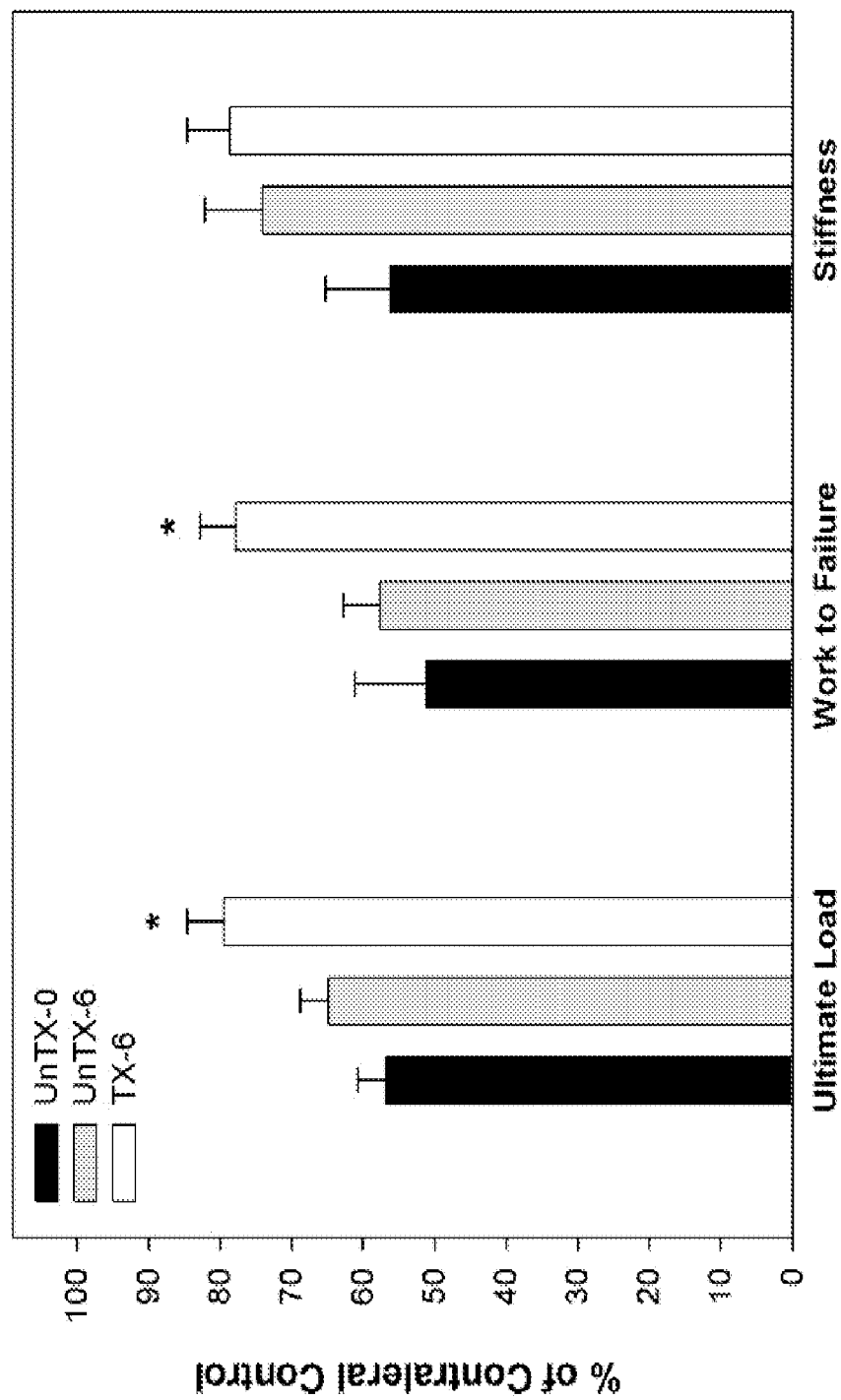
FIG. 6 shows biomechanical properties for ligaments with partial ACL injuries at time zero (UnTx-0), at six weeks with no treatment (UnTx-6) and at six weeks after treatment of the defect with a collagen-PRP scaffold (Tx-6). All values are percentage of intact contralateral control.

Mechanical Testing:

There was a 40% increase in failure strength between zero and six weeks in the treatment group (0.80–0.57/0.57), a difference which was statistically significant ($p<0.01$). During the same period, the untreated control group had only a 14% increase in failure strength (0.65-0.57/0.57), a difference which was not statistically significant ($p>0.25$) (FIG. 6). Treatment also affected the normalized work to failure (F-test=3.5, $p<0.05$). For the treated group, the work to failure was 53% greater (0.78-0.51/0.51) than that for the dogs at time zero (UnTX-0) ($p=0.02$), but the 35% difference between the treated (TX-6) and untreated dogs (UnTX-6) at 6 weeks was not statistically significant ($p=0.08$), perhaps reflecting the small number of animals in each of these groups.

This EXAMPLE shows that use of a biomaterial can prevent the progression of a partial ACL injury to a complete injury.

Example 5

Prevention and Inhibition of Development of Cartilage Lesions after a Complete ACL Tear with Biomaterial Treatment ACL injuries place the patient at high risk for post-traumatic osteoarthritis, and the current treatment gold standard, ACL reconstruction, appears not to reduce this risk [4]. "Bio-enhanced" ACL repair, in which a bioactive scaffold is used to stimulate healing of a transected ACL, has been shown to result in similar biomechanical properties when compared to traditional ACL reconstruction in the pig model after 3 months [3]. Bio-enhanced ACL reconstruction, in which the bioactive scaffold is applied to the graft, also shows considerable promise in short term studies [1]. The long-term results of these techniques and the effects of the bio-enhancement on the articular cartilage integrity have not been evaluated and the objective of the present study. This study shows that the structural (tensile) properties of the ligament/graft at 6 and 12 months after injury are equivalent when treated with bio-enhanced ACL repair (BE-repair), bio-enhanced ACL reconstruction (BE-ACLR), or traditional ACL reconstruction (ACLR), and all treatments yield results superior to untreated ACL transection (ACLT). It also shows We that macroscopic cartilage damage following BE-repair is less than traditional ACLR and untreated ACLT.

Methods

All procedures were approved by the animal care and use committee. 62 late adolescent Yucatan mini-pigs underwent unilateral ACL transection and were randomization to four experimental groups: 1) no treatment (ACLT), 2) traditional ACLR, 3) BE-ACLR using a bioactive scaffold, and 4)

Figure 7:
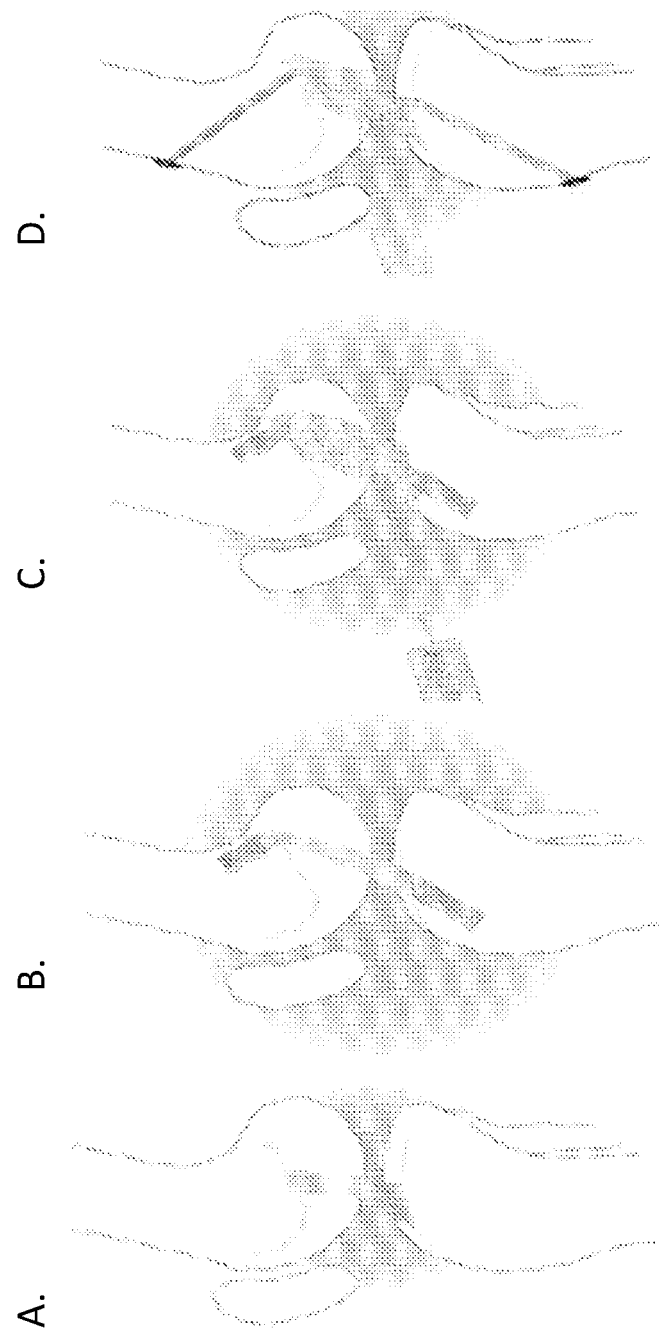
FIG. 7 depicts four treatment groups evaluated in the studies described herein to show that the biomaterial described herein prevents the development of post-traumatic osteoarthritis: A) ACL transection, B) conventional ACL reconstruction (ACLR), C) bio-enhanced ACL reconstruction (BE-ACLR), and D) bio-enhanced ACL repair (BE-Repair).

BE-repair using the same bioactive scaffold (FIG. 7). The bioactive scaffolds (MIACH, Boston Children's Hospital, Boston, Mass.) were manufactured as previously described [2] and contained collagen, glycosaminoglycan, calcium, platelets, red blood cells, plasma and white blood cells.

Preparation of the Extra-Cellular Matrix Scaffold

The bioactive scaffolds (ECM, Boston Children's Hospital, Boston Mass.) were manufactured as previously described. See, e.g., Magarian E M, et al., *Am J Sports Med.* 2010; 38:2528-2534. A slurry of extracellular matrix proteins was produced by solubilizing bovine connective tissue. The collagen concentration was adjusted to a minimum of 10 mg/ml and lyophilized. For the bio-enhanced ACL reconstruction group, the scaffold was a porous hollow cylinder with an outer diameter of 22 mm, inner diameter of 10 mm, and length of 30 mm. See, e.g., Magarian, et al., 2010. For the bio-enhanced ACL repair group, the scaffolds were a porous cylinder 22 mm in diameter and 30 mm long. See, e.g., Elsaid K A, et al., *Arthritis Rheum.* 2008; 58:1707-1715. All sponges were stored at −20° C. until the day of surgery. When implanted in the joint, the bioactive scaffolds were activated with the addition of platelets.

The bioactive scaffold can contain calcium as described herein. It can also be treated to remove or reduce the levels of nucleic acids, phospholipids, GAGs, endotoxins, active pepsin, and/or active virus following the procedures described in Examples 6 and 7 below or those known in the art. Further, the pH value and/or osmolarity of the bioactive scaffold can be adjusted as described herein.

Half the animals in each group were allowed to heal for 6- and 12-months following surgery. The structural properties (i.e., yield load, maximum load, linear stiffness) of the ligament/graft of both legs were measured following an established standardized protocol [3]. The length and width of all lesions on the cartilage surfaces were also assessed using calipers following application of India ink to highlight the lesions. Lesion areas were estimated assuming an elliptical fit and summed across compartments for each joint. Generalized estimating equations were used to statistically model the structural properties and total cartilage lesion area data in both the surgical and contralateral ACL intact joints while considering the four experimental conditions and time of healing.

Surgical Technique: ACL Transection

A medial arthrotomy was created and the fat-pad partially resected to expose the ACL. The ACL was cut between the proximal and middle thirds of the ligament with a scalpel. A Lachman test was performed to verify ACL transection. The knee was then irrigated with 500 cc of normal saline. For those animals assigned to receive no treatment, the incision was closed in layers as previously described. See, e.g., Scheffler S U, et al., *Arthroscopy.* 2008; 24:448-458.

Surgical Technique: ACL Reconstruction and Bio-Enhanced ACL Reconstruction

Following ACL transection, an ACL reconstruction procedure was performed using fresh-frozen bone-patellar tendon-bone allografts harvested from age, weight, and gender matched donor animals as previously described.[14] The entire patellar tendon (~10 mm in width) was used for the soft tissue portion of the graft while the bone plugs were trimmed to 7 mm diameter. Femoral graft fixation was achieved with a 6×20 mm bio-absorbable interference screw (Biosure; Smith & Nephew, Andover, Mass.). The graft was then manually pre-conditioned in tension twenty times. For the animals in the ACL reconstructed group, the grafts were firmly tensioned with the knee in maximal extension (30°) and the distal block was secured in the tibia using a second 6 mm interference screw. An extracortical tibial button was used for supplemental tibial fixation. The incision was closed in layers.

For the animals in the bio-enhanced ACL reconstruction group, the same ACL reconstruction procedure was performed; however, just after femoral graft fixation, the hollow cylindrical extracellular matrix based scaffold was threaded onto the graft and positioned to cover the intra-articular soft tissue portion. The distal bone plug was seated retrograde into the tibial tunnel and fixed to the tibia using a 6 mm interference screw backed with an extracortical tibial button. Three cubic centimeters of autologous blood were used to saturate and activate the scaffold in situ. The scaffold-blood composite was confined within the intercondylar notch and did not extend over the articular surfaces. The collagen-blood composite was allowed to set for a minimum of 10 minutes before completing the surgical procedure.

Surgical Technique: Bio-Enhanced ACL Repair

Bio-enhanced ACL repair was performed as previously described. Magarian E M, et al., *Am J Sports Med.* 2010; 38:2528-2534. In brief, an Endobutton carrying three looped sutures was passed thru a 4 mm femoral tunnel and flipped. Two of the sutures were threaded through the scaffold, into a predrilled tibial tunnel and fixed extracortically using a button with the knee in maximum extension (30°). The remaining suture was tied to a Kessler suture of #1 Vicryl (Ethicon, Somerville, N.J.) which had been placed in the tibial stump of the ACL. (FIG. 7). Three cc of autologous blood containing platelets were used to saturate the scaffold in situ. The incisions were closed in layers after ten minutes.

All incisions were closed in layers. Following surgery, all animals were housed for four weeks in individualized pens and were then shipped to a farm for long-term porcine care (Coyote Consulting Corporation Inc, Douglas, Mass.). After 6- and 12-months of healing, the animals were euthanized and the limbs harvested. The knees were immediately frozen at −20° C. until mechanical testing.

Results

Figure 8:
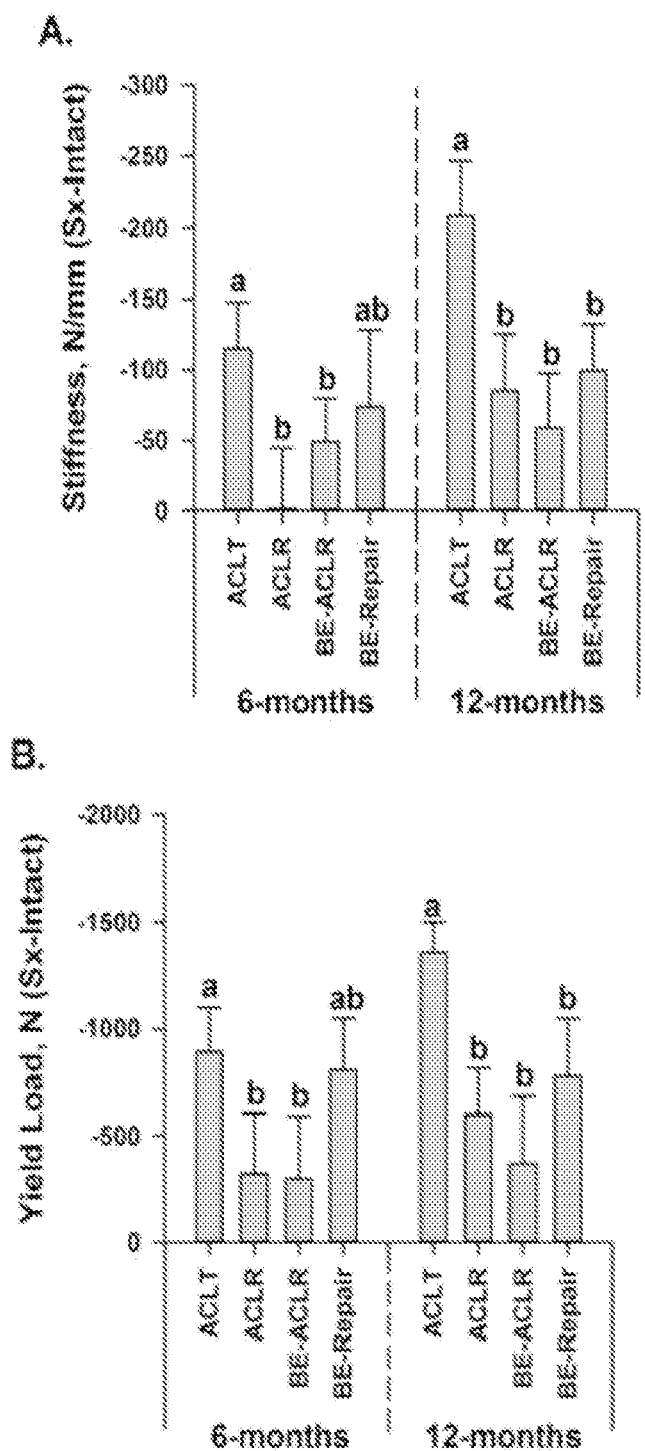
FIG. 8 is a graph the mean differences between limbs (Surgical-Intact) for A) linear stiffness, B) yield load, and C) maximum load for the four experimental groups (ACLT=ACL transection, ACLR=ACL reconstruction, BE-ACLR=bio-enhanced ACL reconstruction and BE-Repair=bio-enhanced ACL repair) at 6 and 12 months. The mean data are plotted with the 95% confidence intervals. A value of zero indicates that the yield or maximum failure loads are equal between legs. Means that do not differ between groups after Holm adjustment within each time point have the same lower case letter (a or b).
Figure 8:
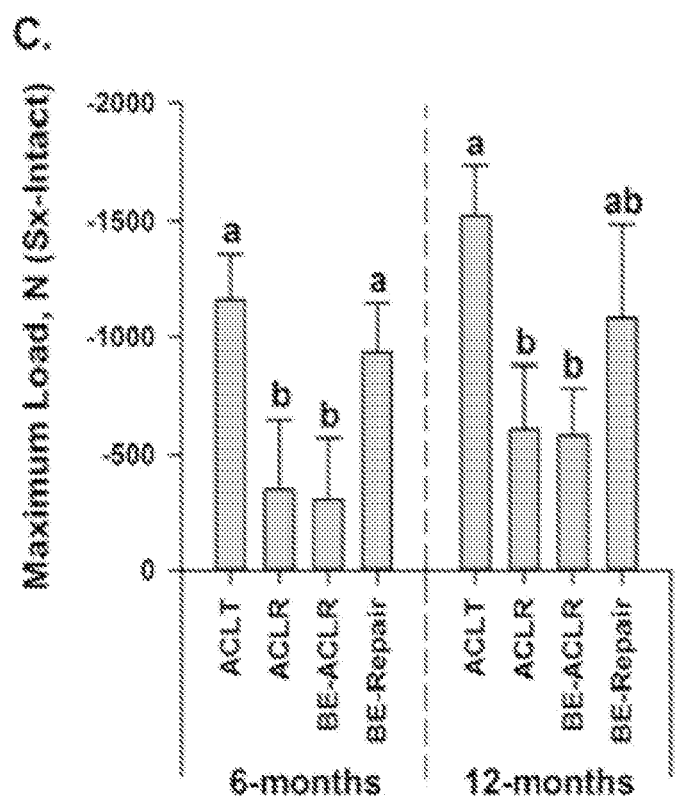

For all treatment groups and both time points, the structural properties (yield load, maximum load, and linear stiffness) were significantly less than the contralateral ACL intact knee (p<0.01). After 12 months, the normalized yield load and linear stiffness for BE-repair, BE-ACLR and traditional ACLR were significantly greater (p<0.01) than the ACLT group but equivalent (p>0.29) to each other (FIG. 8). The AP laxity data for both the surgical and contralateral uninjured knees are provided in Table 4.

Figure 9:
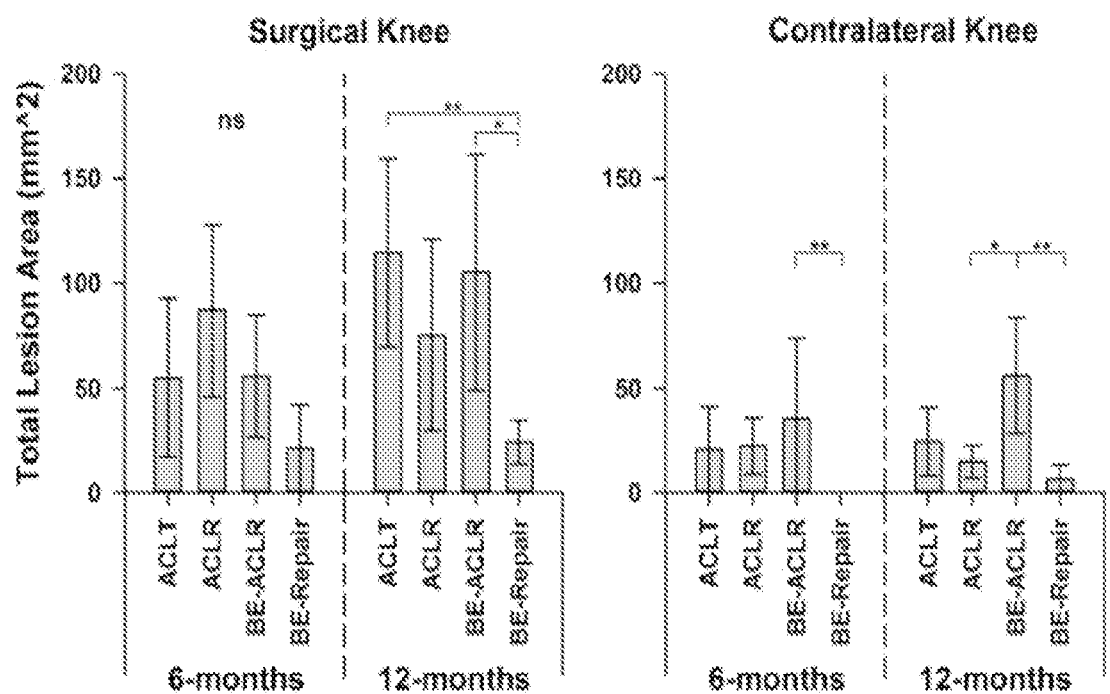
FIG. 9 depicts the mean total lesion areas for the four experimental groups (ACLT=ACL transection, ACLR=ACL reconstruction, BE-ACLR=bio-enhanced ACL reconstruction and BE-Repair=bio-enhanced ACL repair) at 6 and 12 months for the surgical and the ACL intact knee.

Cartilage lesion areas after BE-repair were significantly less than that following BE-ACLR, traditional ACLR and untreated ACLT at 12 months (FIG. 9). It is interesting to note that there was a significant treatment effect in the articular cartilage of the contralateral knee (FIG. 9). When the groups were normalized by the contralateral knee, the groups with the lowest cartilage damage were those treated with the bio-active scaffold (bio-enhanced repair and bio-enhanced reconstruction) demonstrating the role of this material in preventing the development of post-traumatic osteoarthritis after an ACL injury. In addition, several of the animals in these groups were noted to have a concomitant cartilage injury at the time of the ACL injury, and these lesions were not seen after treatment with the bio-active scaffold, suggesting a role for this scaffold in treating articular cartilage defects.

The bioactive scaffold, which is based on the extracellular matrix proteins found in the normal ACL, absorbs the patient's own blood and results in the platelets within the blood releasing anabolic growth factors including PDGF, FGF-2 and TGF-b into the wound site (FIG. 7).

Cartilage Assessment

Figure 10:
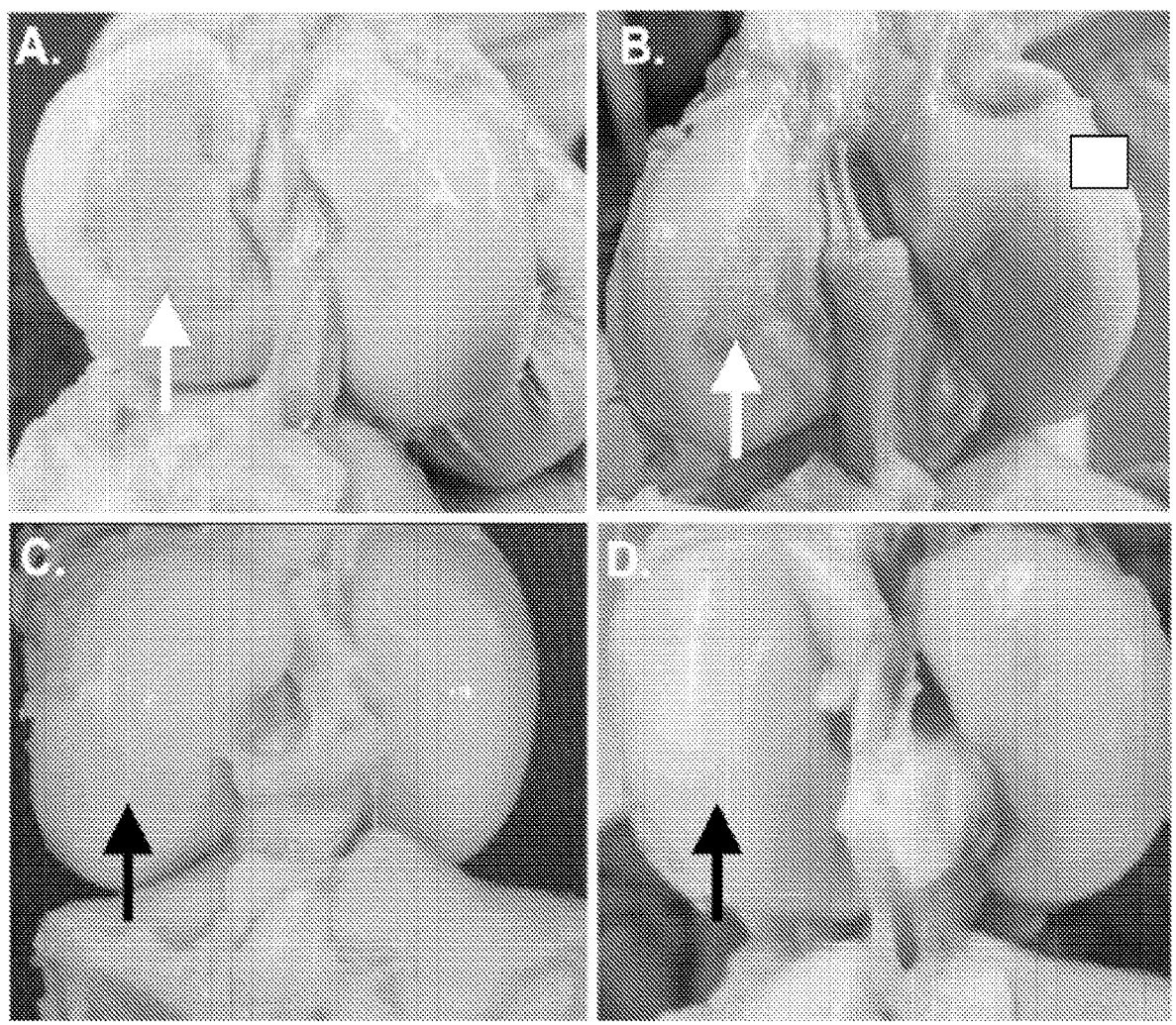
FIG. 10 is a photograph depicting the distal femur cartilage 1-year after A) an untreated ACL rupture, B) after conventional ACL reconstruction, C) after bio-enhanced ACL repair, and D) after bio-enhanced ACL reconstruction. Note the damage to the medial femoral condyle in the untreated and ACL reconstructed knees (white arrows) and the lack of damage in the medial femoral condyle in the bio-enhanced ACL repair and bio-enhanced ACL reconstructed knees (black arrows).

There were no significant differences in the lesion areas of the surgical limbs between the four experimental groups 6 months post-operatively ($p_{adj}$>0.380; FIG. 9). However, at 12 months, the mean lesion area for the bio-enhanced ACL repair knees was significantly less than the ACL transected knees ($p_{adj}$=0.0017) and the ACL reconstructed knees ($p_{adj}$=0.0677) (FIG. 9), and when normalized by the contralateral side, both the bio-enhanced repair group and the bio-enhanced ACL reconstruction group had no significant cartilage loss at 12 months after surgery (FIG. 9), whereas significant loss (mean of over 40 square millimeters) was seen in both the ACL transected and ACL reconstructed knees. Comparisons between the total macroscopic scores between groups and knees followed similar trends to those of the lesion area measurements. The results also supports that the macroscopic cartilage damage of the tibiofemoral joint following bio-enhanced ACL repair is less following untreated ACL transection, and a strong trend to be less than conventional ACL reconstruction (p=0.068) at 12 months (FIGS. 9 and 10).

Discussion

The results obtained from this study support that the structural properties of the ligament following BE-repair were similar to BE-ACLR, traditional ACLR, and superior to untreated ACLT after 12-months of healing. The results also show support that the macroscopic cartilage damage following BE-repair was less than traditional ACLR and untreated ACLT at 12 months, and when the data was normalized to the contralateral knee, both the bio-enhanced repair group and the bio-enhanced reconstruction group had the lowest amount of cartilage damage after the ACL injury. Taken together, these results indicate that the collagen material as described herein can reduce the risk for developing, delay or prevent the onset of post-traumatic osteoarthritis.

REFERENCES

1. Fleming B C, et al., *Am J Sports Med.* 2009; 37:1554-1563.
2. Murray M M, et al., *J Bone Joint Surg Am.* 2010; 92:2039-2049.
3. Vavken P, et al., *Arthroscopy.* 2012; 28:672-680.
4. Von Porat A, et al., *Ann Rheum Dis.* 2004; 63:269-273.

Example 6

Terminal Sterilization of ECM Scaffold Using Ethylene Oxide or Electron Beam Sterilization In this example, the ECM scaffold described herein is terminally sterilized by ethylene oxide (EO) or electron beam (E-beam) sterilization and the outcomes of these sterilization processes are compared with respect to scaffold characteristics.

EO Sterilization

For the ethylene oxide groups, lyophilized ECM scaffolds were placed into gas permeable pouches and subjected to EO sterilization. Each pouch was marked with the EO sterilization indicator to confirm the EO sterilization.

E-Beam Sterilization

For the E-beam groups, ECM scaffolds as described herein are placed in glass vials that were capped and sealed using plastic stoppers, crimped using an aluminum clamping system. The packaging of the scaffold samples is similar to the image shown in FIG. 11; glass vials with rubber stoppers which are sealed on top via aluminum sealing system.

Figure 11:
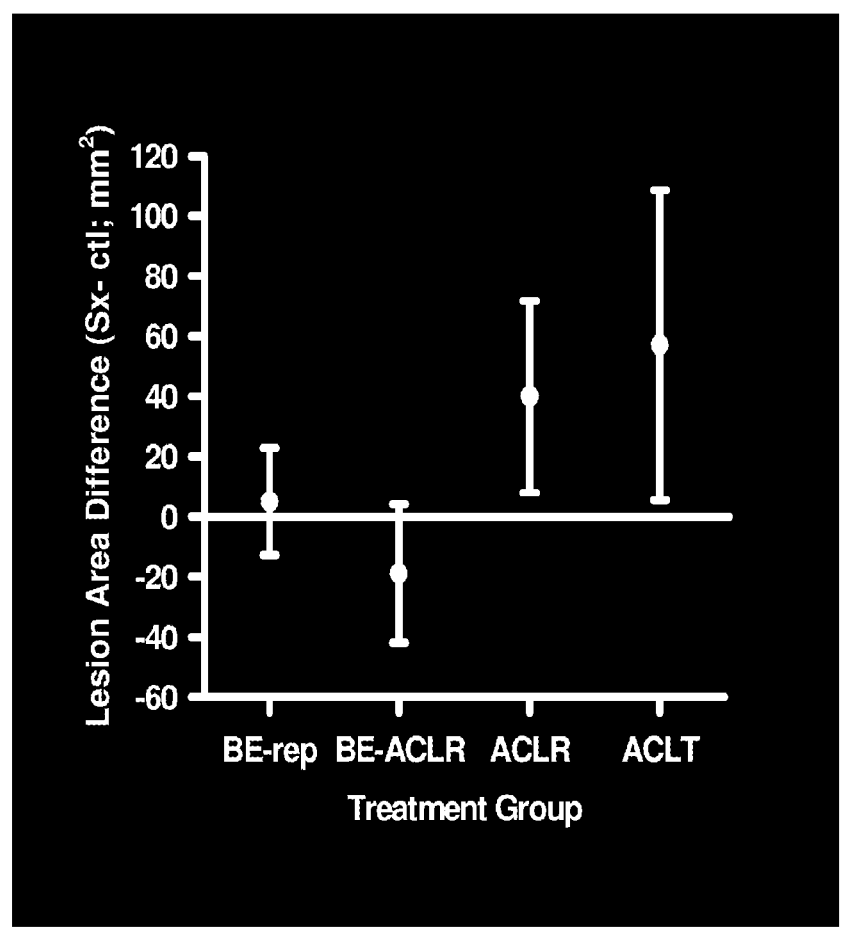
FIG. 11 is a graph showing the size of the articular cartilage lesions that develop in porcine knees one year after ACL transection and no treatment (group A), treatment with standard ACL reconstruction (no biomaterial)(group B), and treatment with ACL reconstruction and the biomaterial (BE-ACL, group C), as well as suture repair using the biomaterial (BE-Repair, group D).
Figure 12:
FIG. 12 is a photograph showing initial packaging set up of an ECM Scaffold (e.g., a collagen scaffold) for e-beam treatment.

ECM Scaffold samples are prepared and used as follows. Samples were prepared by lyophilizing bovine connective tissue, washing the tissue, digesting in pepsin and then lyophilizing in a mold to make a cylindrical scaffold. The ECM scaffold samples thus prepared are placed inside glass vials, which are purged by Nitrogen in order to reduce the amount of the oxygen in them. All of the glass vials are sealed and clamped as shown in FIG. 11. The sealed glass vials will be kept on dry ice during sterilization.

The ECM scaffold samples are subjected to 15 kGy E-Beam sterilization process under the following conditions:

(i) Temperature; sterilization under frozen condition on dry ice
(ii) Presence of Oxygen; the vial containing ECM Scaffold will be free of oxygen (Nitrogen purged)
(iii) Dosage; 15 kGy A group of non-sterilized ECM scaffolds, which are treated in the same manner as the E-beam group except for the E-beam sterilization is used as an "e-beam" control group.

Following the sterilization processes, the ECM Scaffolds went through a series of tests alongside the control non-sterile ECM Scaffold to determine whether the sterilization process had changed the ECM Scaffold characteristics.

TABLE 4

The mean (95% Confidence Limits) for the linear stiffness (stiffness), yield load and maximum load and AP laxity at 30° (AP30), 60° (AP60), and 90° (AP90) of flexion for the four treatment groups; ACL transection (ACLT), ACL reconstruction (ACLR), bio-enhanced ACL reconstruction (BE-ACLR), and bio-enhanced ACL repair (BE-repair), at 6 and 12 months after surgery.

| | ACLT | | ACLR | | BE-ACLR | | BE-repair | |
|---|---|---|---|---|---|---|---|---|
| | Surgical | Intact | Surgical | Intact | Surgical | Intact | Surgical | Intact |
| 6 Month | | | | | | | | |
| Stiffness (kN/mm) | 0.09 (0.06-0.12) | 0.20 (0.19-0.22) | 0.22 (0.19-0.24) | 0.22 (0.21-0.25) | 0.18 (0.16-0.20) | 0.23 (0.21-0.25) | 0.12 (0.08-0.16) | 0.20 (0.16-0.23) |
| Yield Load (kN) | 0.37 (0.26-0.48) | 1.26 (1.13-1.39) | 1.18 (0.90-1.46) | 1.49 (1.29-1.71) | 1.20 (0.96-1.43) | 1.50 (1.39-1.61) | .56 (0.36-0.75) | 1.36 (1.23-1.49) |
| Maximum Load (kN) | 0.38 (0.27-0.49) | 1.54 (1.43-1.64) | 1.26 (0.97-1.55) | 1.61 (1.43-1.79) | 1.29 (1.02-1.55) | 1.59 (1.45-1.73) | 0.60 (0.43-0.78) | 1.54 (1.42-1.65) |
| CSA (mm$^2$) | 36 (20-65) | 34 (26-43) | 84 (75-94) | 29 (27-32) | 78 (57-107) | 31 (22-45) | 54 (38-76) | 31 (28-34) |
| AP30 (mm) | 4.7 (3.7-6.1) | 2.8 (2.2-3.6) | 2.2 (1.8-2.5) | 2.4 (1.8-3.2) | 2.5 (1.8-3.4) | 1.7 (1.2-2.4) | 3.6 (2.5-5.1) | 2.7 (2.3-3.2) |

TABLE 4-continued

The mean (95% Confidence Limits) for the linear stiffness (stiffness), yield load and maximum load and AP laxity at 30° (AP30), 60° (AP60), and 90° (AP90) of flexion for the four treatment groups; ACL transection (ACLT), ACL reconstruction (ACLR), bio-enhanced ACL reconstruction (BE-ACLR), and bio-enhanced ACL repair (BE-repair), at 6 and 12 months after surgery.

|  | ACLT | | ACLR | | BE-ACLR | | BE-repair | |
| --- | --- | --- | --- | --- | --- | --- | --- | --- |
|  | Surgical | Intact | Surgical | Intact | Surgical | Intact | Surgical | Intact |
| AP60 (mm) | 8.8 (7.4-10.4) | 3.5 (3.2-3.8) | 7.7 (6.7-8.8) | 3.0 (2.8-3.3) | 6.5 (5.0-8.4) | 3.0 (2.5-3.6) | 8.5 (7.4-9.8) | 3.0 (2.7-3.4) |
| AP90 (mm) | 6.9 (5.7-8.2) | 2.7 (2.4-3.1) | 8.1 (6.4-10.2) | 2.1 (1.9-2.4) | 7.8 (6.4-9.5) | 2.1 (1.8-2.5) | 7.1 (6.4-7.7) | 2.2 (2.1-2.4) |
| 12 Month | | | | | | | | |
| Stiffness (kN/mm) | 0.07 (0.04-0.11) | .28 (.27-.29) | 0.18 (0.13-0.22) | 0.26 (0.23-0.28) | 0.21 (0.17-0.25) | 0.27 (0.25-0.28) | 0.15 (0.12-0.18) | 0.25 (0.23-0.27) |
| Yield Load (kN) | 0.20 (0.11-0.29) | 1.56 (1.43-1.67) | 0.93 (0.67-1.18) | 1.52 (1.30-1.74) | 0.96 (0.72-1.21) | 1.33 (1.12-1.54) | 0.57 (0.42-0.72) | 1.35 (1.16-1.53) |
| Maximum Load (kN) | 0.26 (0.14-0.38) | 1.78 (1.62-1.95) | 1.17 (1.31-2.19) | 1.78 (1.65-1.90) | 1.17 (0.90-1.43) | 1.74 (1.59-1.90) | 0.71 (0.46-0.97) | 1.79 (1.58-2.00) |
| CSA (mm$^2$) | 22 (7-69) | 26 (23-29) | 66 (48-91) | 30 (25-35) | 55 (43-68) | 30 (24-36) | 59 (39-89) | 29 (23-37) |
| AP30 (mm) | 6.0 (4.4-8.1) | 2.2 (1.8-2.8) | 2.8 (2.2-3.5) | 2.4 (2.1-2.7) | 2.8 (1.9-4.1) | 2.4 (1.9-3) | 4.2 (2.7-6.6) | 2.9 (2.3-3.7) |
| AP60 (mm) | 9.9 (8.8-11.2) | 3.0 (2.6-3.5) | 6.2 (4.6-8.4) | 3.1 (2.8-3.4) | 6.6 (4.8-9.2) | 2.8 (2.3-3.4) | 8.8 (8.1-9.7) | 3.2 (2.7-3.9) |
| AP90 (mm) | 7.5 (6.5-8.8) | 1.9 (1.7-2.2) | 8.9 (7.2-11.0) | 2.4 (2.2-2.6) | 7.2 (5.2-10) | 2.6 (2.2-3) | 8.0 (7.5-8.7) | 2.3 (2-2.6) |

Example 7

Methods for Lowering DNA/RNA/Cell Components in Biomaterials

In this experiment, tissues from 8 bovine knees were collected. The total wet weight of the harvested tissues was 166.5 g. The tissues were lyophilized until dry and then homogenized. The homogenized tissue was then divided into 16 samples. The dry tissue samples were then rinsed in 2% antibiotic solution overnight.

Start of Differentiation:

Following the antibiotic rinse, the samples were divided into 16 different treatment groups as noted below.

Summary of Sample Groups:

Sample 1:

The tissue was rinsed with NaCl solution followed by ultrapure water three times, and then washed with citrate buffer with a pH=4.0 for 72 hours. The samples were ultracentrifuged and treated with pepsin and 0.01N HCl. The amount of pepsin and HCl was determined using the wet weight of the sample. The remaining sample was tested.

Sample 2:

The tissue was rinsed with NaCl solution followed by ultrapure water three times. The samples were ultracentrifuged and treated with pepsin and HCl. The amount of pepsin and HCl was determined using the wet weight of the sample. The remaining sample was tested.

Sample 3:

The tissue was rinsed with NaCl solution followed by ultrapure water. The sample was then treated with sterile RNase A (100 μg/mL) and DNase I (150 IU/mL) with 10 mmol MgCl$_2$, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 4:

The tissue was rinsed with NaCl solution followed by ultrapure water. The sample was then treated with sterile RNase A (100 μg/mL) and DNase I (150 IU/mL) with 10 mmol MgCl$_2$, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 5:

The tissue was rinsed NaCl solution followed by ultrapure water. The sample was then treated with sterile RNase A (100 μg/mL) and DNase I (150 IU/mL) with 10 mmol MgCl$_2$, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 6:

The tissue was rinsed with NaCl solution followed by ultrapure water. The sample was then treated with sterile RNase A (100 μg/mL) and DNase I (150 IU/mL) with 10 mmol MgCl$_2$, in 0.05M Tris-Buffer (pH=7.5). The samples were ultracentrifuged and treated with pepsin and HCl. The amount of pepsin and HCl was determined using the wet weight of the sample. The remaining sample was tested.

Sample 7:

The tissue was rinsed with ultrapure water. The sample was then treated with sterile RNase A (100 μg/mL) and DNase I (150 IU/mL) with 10 mmol MgCl$_2$, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 8:

The tissue was rinsed with ultrapure water. The sample was then treated with sterile RNase A (100 μg/mL) and DNase I (150 IU/mL) with 10 mmol MgCl2, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 9:

The tissue was rinsed with ultrapure water. The sample was then treated with sterile RNase A (100 μg/mL) and DNase I (150 IU/mL) with 10 mmol MgCl2, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 10:

The tissue was rinsed with ultrapure water. The sample was then treated with sterile RNase A (100 μg/mL) and DNase I (150 IU/mL) with 10 mmol $MgCl_2$, in 0.05M Tris-Buffer (pH=7.5). The samples were ultracentrifuged and treated with pepsin and HCl. The amount of pepsin and HCl was determined using the wet weight of the sample. The remaining sample was tested.

Sample 11:

The sample was treated with sterile RNase A (100 μg/mL) and DNase I (150 IU/mL) with 10 mmol $MgCl_2$, in 0.05M Tris-Buffer (pH=7.5) and then washed with citrate buffer with a pH=4.0 for 72 hours. The tissue was then again rinsed with NaCl solution. The samples were ultracentrifuged and treated with pepsin and HCl. The amount of pepsin and HCl was determined using the wet weight of the sample. The remaining sample was tested.

Sample 12:

The sample was treated with sterile RNase A (100 μg/mL) and DNase I (150 IU/mL) with 10 mmol $MgCl_2$, in 0.05M Tris-Buffer (pH=7.5). The tissue was then again rinsed with NaCl solution. The samples were ultracentrifuged and treated with pepsin and HCl. The amount of pepsin and HCl was determined using the wet weight of the sample. The remaining sample was tested.

Sample 13:

The sample was treated with sterile RNase A (100 μg/mL) and DNase I (150 IU/mL) with 10 mmol $MgCl_2$, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 14:

The sample was treated with sterile RNase A (100 μg/mL) and DNase I (150 IU/mL) with 10 mmol $MgCl_2$, in 0.05M Tris-Buffer (pH=7.5). The samples were ultracentrifuged and treated with pepsin and HCl. The amount of pepsin and HCl was determined using the wet weight of the sample. The remaining sample was tested.

Sample 15:

The tissue was rinsed with NaCl solution followed by ultrapure water. The sample was then treated with TritonX-Sodium deoxycholate-PBS solution at 0 to 25 degrees C. for at least 24 hours. The tissue was rinsed and then treated with sterile RNase A (100 μg/mL) and DNase I (150 IU/mL) with 10 mmol $MgCl_2$, in 0.05M Tris-Buffer (pH=7.5) and then washed with citrate buffer with a pH=4.0 for 72 hours. The samples were ultracentrifuged and treated with pepsin and HCl. The amount of pepsin and HCl was determined using the wet weight of the sample. The remaining sample was tested.

Sample 16:

The tissue was rinsed with NaCl solution followed by ultrapure water. The sample was then treated with TritonX-Sodium deoxycholate-PBS solution at 0 to 25 degrees C. for at least 24 hours. The tissue was rinsed and then treated with sterile RNase A (100 μg/mL) and DNase I (150 IU/mL) with 10 mmol $MgCl_2$, in 0.05M Tris-Buffer (pH=7.5). The samples were ultracentrifuged and treated with pepsin and HCl. The amount of pepsin and HCl was determined using the wet weight of the sample. The remaining sample was tested.

Figure 13:
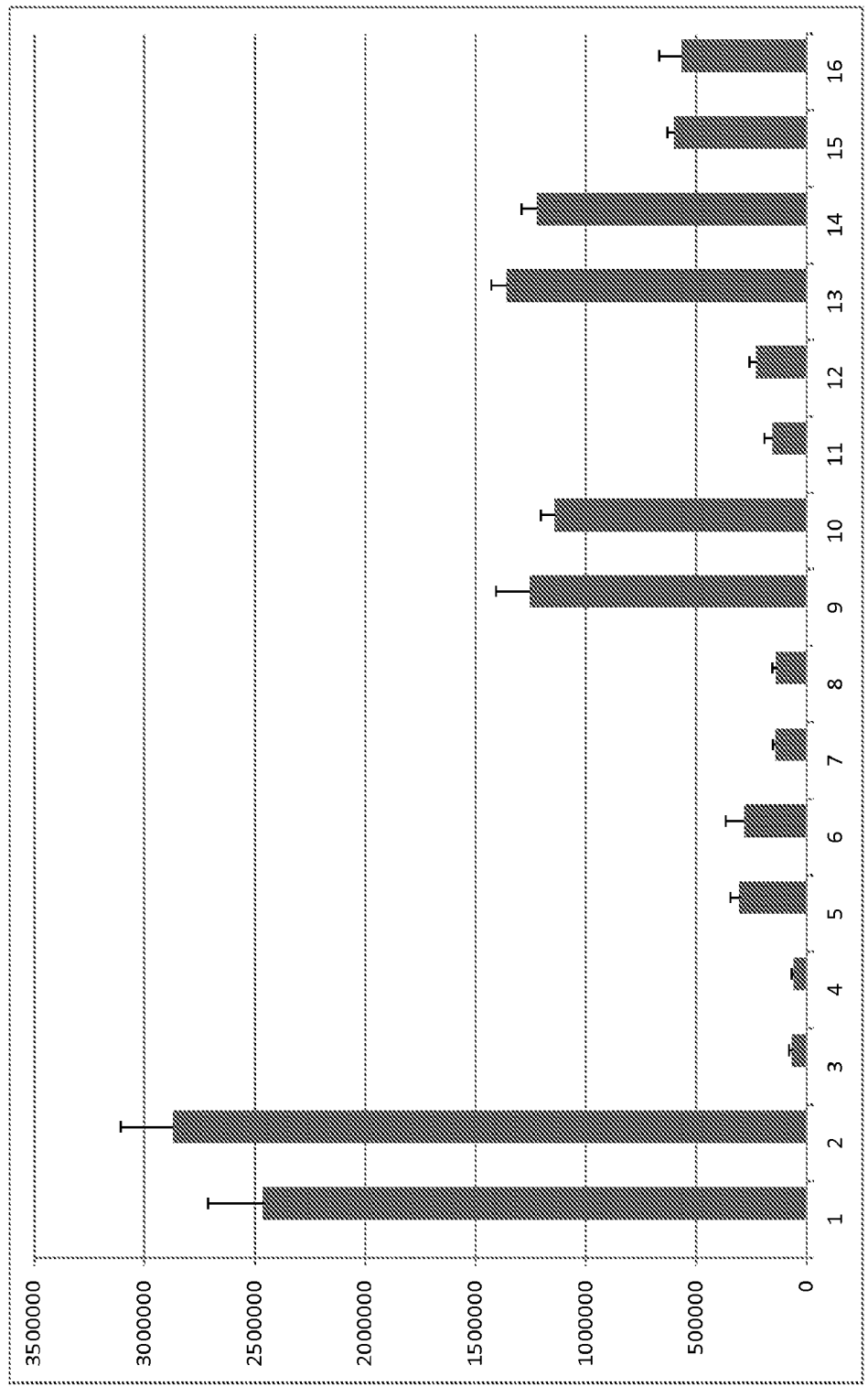
FIG. 13 is a chart showing DNA content in samples treated as described in Example 7 below.

DNA contents of the treated samples as described above were determined. As shown in FIG. 13, the y axis is ng of DNA per gram of collagen formulation, and the x axis is the sample designation as noted above. These data show the relative efficacy of the citrate rinse (samples 4, 6, 11) and the DNAse/RNAse steps (samples 3, 4, 5, 6, 7, 8). Triton X also had some efficacy (Samples 15 and 16). For reference, the DNA content of the native tissue is approximately 500,000 to 3,000,000 ng DNA/g tissue.

The treated samples were compared with those in native tissues and in commercially available scaffolds, using the processing techniques described above. The collagen scaffold described herein was tested against: 1) native tissue, 2) Surgifoam, 3) TissueMend, and 4) Restore. DNA content (FIG. 14, panel A), GAG content (FIG. 14, panel B), and phophatidylcholine content (FIG. 14, panel C) as a measure of retained cellular membrane were investigated. The results are listed below.

Figure 14:
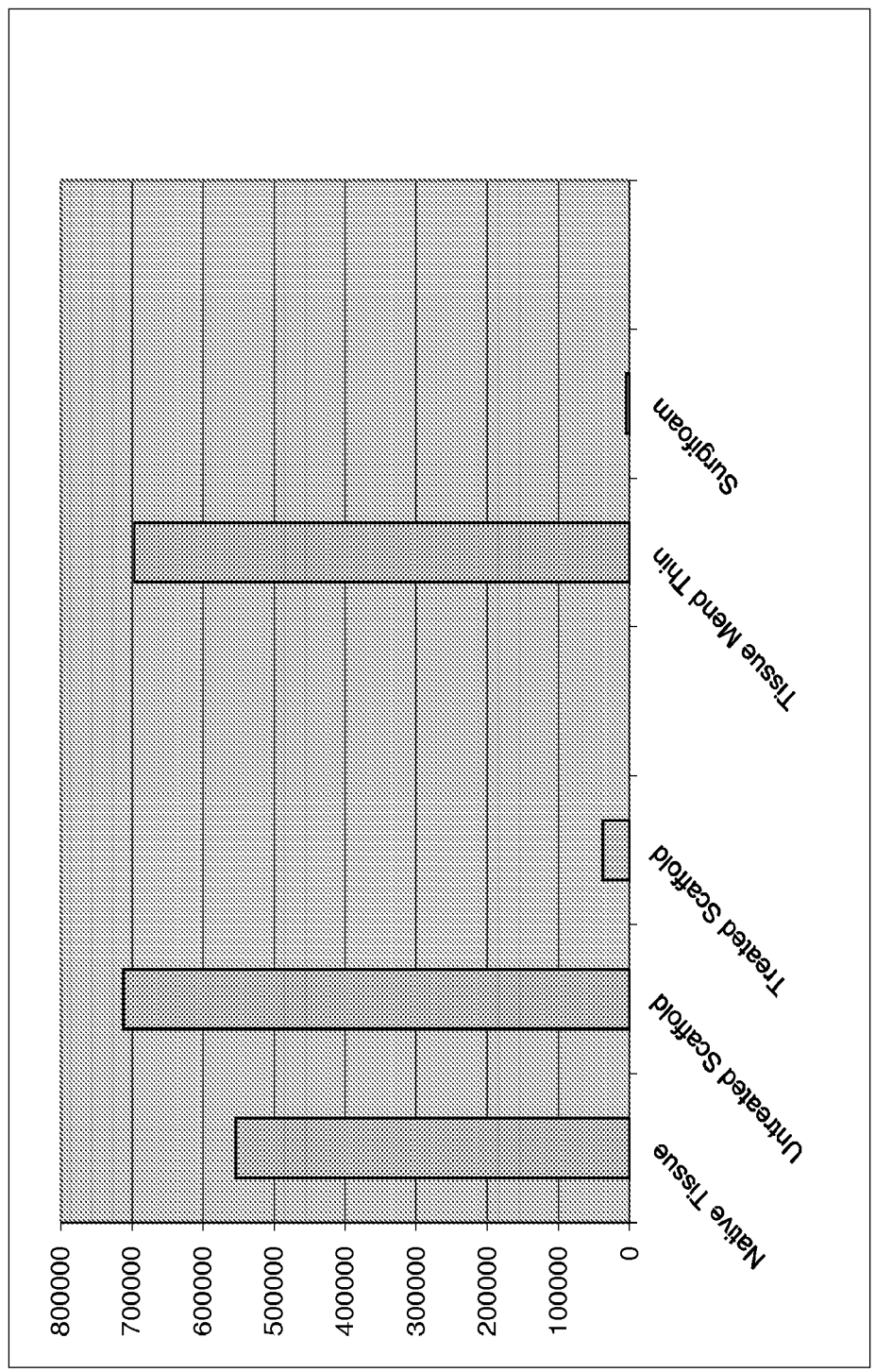
FIG. 14 depicts DNA content (Panel A), GAG content (Panel B), and phospholipid content (Panel C) in samples treated as described in Example 7 below relative to the DNA, GAG, and phospholipid content in native tissues and in commercially available collagen scaffold. In 15A, the y axis the DNA content (ng DNA/g dry tissue or scaffold) for treated and untreated scaffolds in comparison to Native Tissue (no treatment), TissueMend and Surgifoam (two FDA approved scaffolds).
Figure 14:
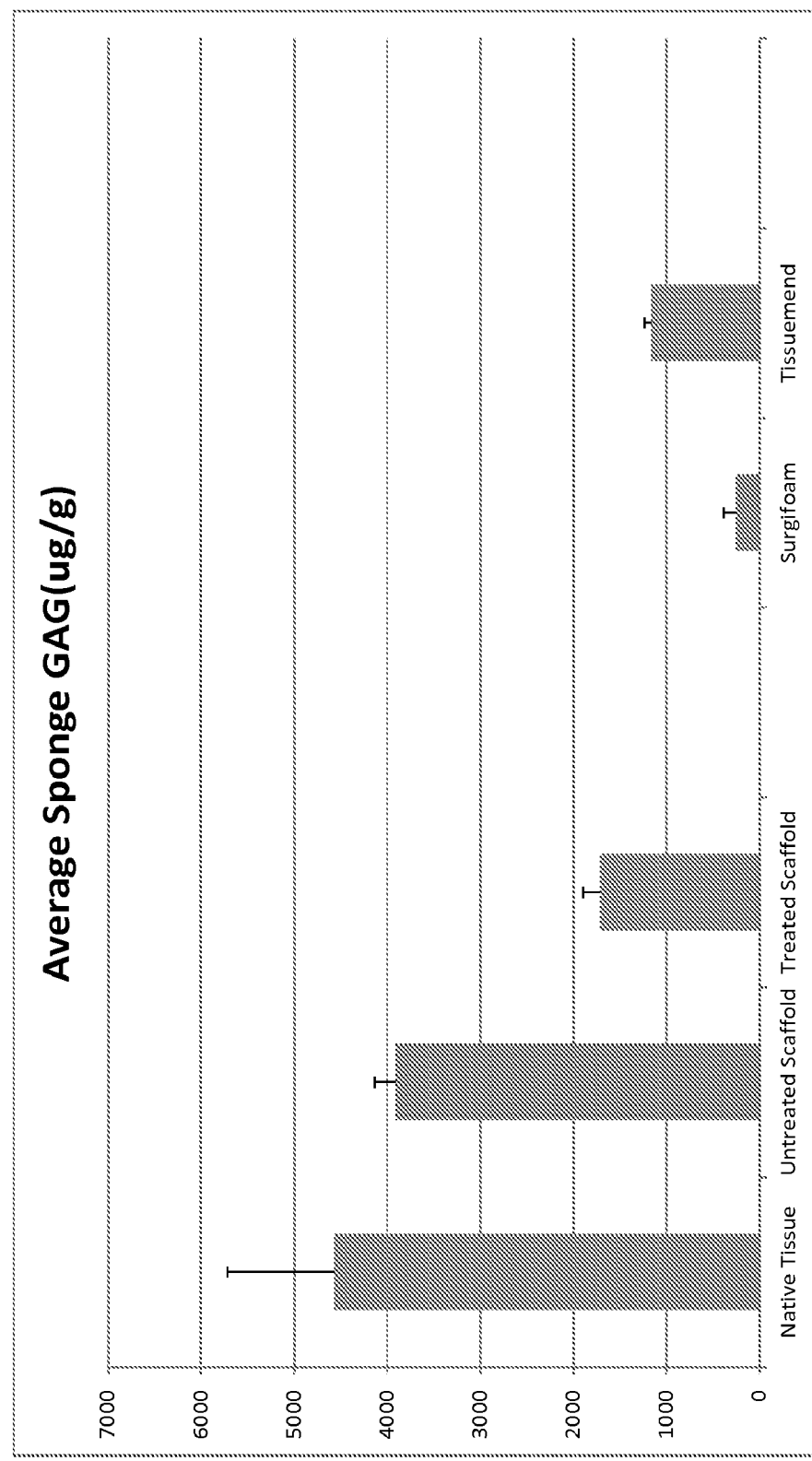
Figure 14:
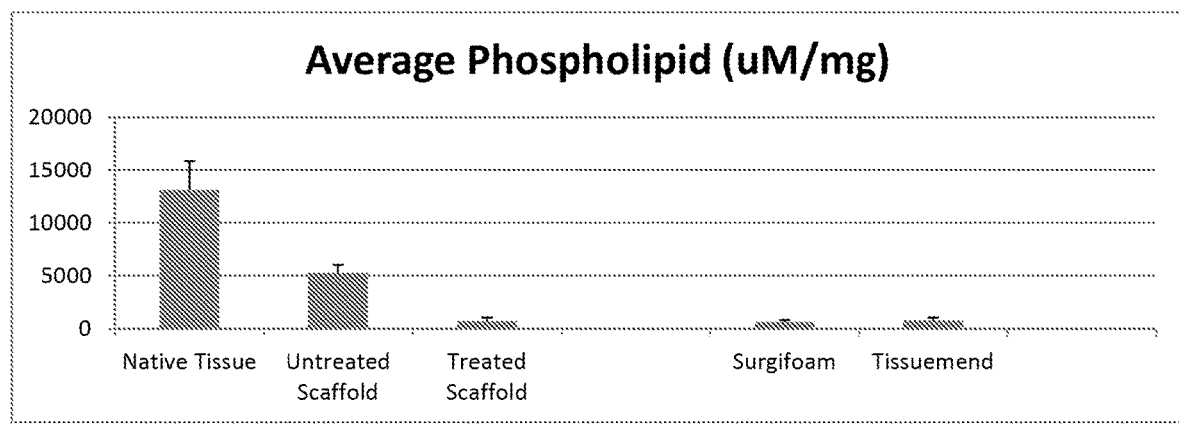

DNA content (ng DNA/g tissue or scaffold) for treated and untreated scaffolds was compared with that in native tissue (no treatment), TissueMend and Surgifoam (two FDA approved scaffolds). The treatment of the scaffold with techniques to remove DNAs as described above reduced the DNA content in the scaffold to less than 20% of that found in the native tissue. FIG. 13 and FIG. 14, panel A.

GAG content (ug GAG/g tissue or scaffold) for treated and untreated scaffolds was compared with that of native tissue (no treatment), TissueMend and Surgifoam (two FDA approved scaffolds). The treatment of the scaffold with techniques described above to remove the GAG reduced the GAG in the scaffold by over 30%. FIG. 14, Panel B.

Phospholipid content (uM/mg) of the native tissue, untreated scaffold and treated scaffold was compared with that in Surgifoam and TissueMend (two FDA approved scaffolds). The treatment of the scaffold with techniques described above to remove the phospholipid reduced the phospholipid in the scaffold to a level less than 20% that found in the native tissue. FIG. 14, panel C.

Example 8

Methods for Neutralizing Pepsin in Biomaterials

Scaffolds were made from extracellular matrix proteins using a pepsin digestion. After digestion, one group had no further treatment, while the second group was treated with a strong base to inactivate the pepsin.

Briefly, a strong base (e.g., KOH or NaOH or LiOH) at a suitable concentration was added into a collagen slurry in a dropwise manner to bring the pH value to above 4.0. Additional strong base was added to bring the pH of the slurry to 7.0 or greater. Once the slurry reached its target pH range, the solution is kept there for a suitable period of time, e.g., 1 to 10 minutes.

After inactivation of the pepsin, the pH of the slurry was returned to a pH between 7.0 and 8.0 by the addition of a buffer with a pK of between 7 and 8, such as a buffer containing TAPSO, HEPES, TES, MOPS, Cacodylate SSC or Succinic acid.

Figure 15:
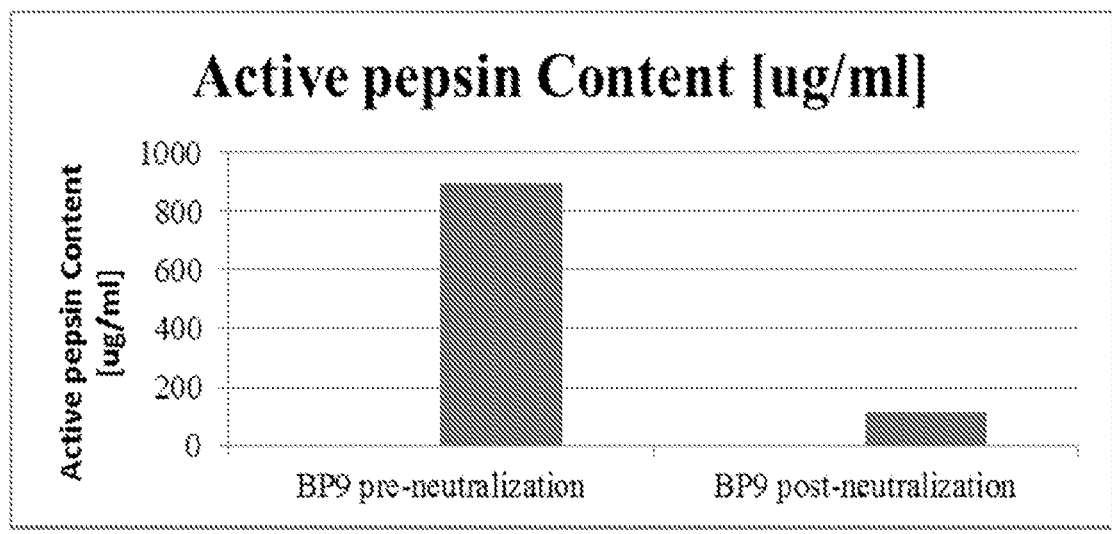
FIG. 15 is a chart showing the level of active pepsin in collagen materials treated as described in Example 8 below.

As shown in FIG. 15, the level of active pepsin in a collagen material reduced by around 80% as compared to the active pepsin level before the inactivation treatment.

Example 9

Testing HDBC Sponge with $CaCl_2$ Added into Collagen Slurry

Preparation:

Five collagen sponges containing three different concentrations of CaCl2 (high, medium and low), were prepared. The sponges were prepared by taking collagen slurry, and adding a 30 mM, 60 mM or 90 mM solution. The slurry was then lyophilized. The sponges were then rehydrated with water to result in a specific collagen concentration. The collagen slurry was neutralized using a buffer with a pK of between 7 and 8 (Cellgro, Mediatech, Inc, Herndon, Va.) and enough 7.5% sodium bicarbonate (Cambrex BioScience Walkersville, Inc., Walkersville, Md.) to neutralize the acidic slurry to a pH of 7.4. Five 1.0 mL aliquots of the each concentration of neutral collagen gel was transferred into wells of a 24-wellplate and warmed until gelation occurred. The gels were then lyophilized to make the collagen-calcium sponges.

Procedure:

0.75 mL platelet-rich plasma (PRP) containing plasma, platelets and an anticoagulant was placed on two sponges of each type to see if a clot formed in the collagen-calcium sponge. Two sponges of each concentration were also compressed and then PRP containing an anticoagulant was added to see if that affected clot formation.

Results:

After 10 minutes, clotting did occur in the 90 mM $CaCl_2$ solution sponge. The lower calcium solutions did not clot as well, but some initial clotting did occur. It did not matter whether or not the sponge was compressed before PRP was added. The collagen sponges with calcium allowed the clot to form within the sponge at all concentrations of calcium, even when the blood components were drawn into a tube containing an anticoagulant. The collagen-calcium was able to cause clotting of the anticoagulated blood product in the absence of any added thrombin.

Example 10

Testing HDBC Sponge with Calcium Added the Second Lyophilization

Preparation:

To make the collagen sponges, acid soluble collagen slurry was lyophilized, and rehydrated with water to have a collagen concentration >10 mg/ml. The collagen slurry was neutralized using HEPES Buffer (Cellgro, Mediatech, Inc, Herndon, Va.) and sodium bicarbonate (Cambrex BioScience Walkersville, Inc., Walkersville, Md.) to neutralize the acidic slurry to a pH of 7.4. The pH neutral collagen gel was incubated at 37 degrees C. to allow for gelation of the collagen hydrogel and self-assembly of the collagen fibers, and the gel was then lyophilized to make a collagen sponge. The collagen sponge was cut into thirds and each third was placed into its own Petri dish. One sponge was covered with a low concentration solution of calcium, one sponge was covered with a medium concentration of calcium, and one sponge was covered with a high concentration of calcium. These three sponges were placed in new Petri dishes and were then placed back into the lyophilizer for three days.

Procedure:

The collagen sponges were removed from the lyophilizer and 0.75 mL of a solution containing an anticoagulant, platelet, plasma and white blood cells was placed on each sponge. After 10 minutes, the sponges were put into a 50 cc test tube, and shaken and vortexed to test their structural rigidity.

Results:

It was found that a clot formed in each of the sponges within 10 minutes of the blood components being added. The collagen sponges with calcium allowed the clot to form within the sponge at all concentrations of calcium, even when the blood components were drawn into a tube containing an anticoagulant. The collagen-calcium was able to cause clotting of the anticoagulated blood product in the absence of any added thrombin.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for treating arthritis, comprising: forming a liquid composition by mixing together a collagen material, a calcium solution having a calcium concentration of about 30 mM to about 90 mM, and a red blood cell, wherein the collagen material is a dry powder, and wherein the composition comprises glycosaminoglycan (GAG) in an amount of less than 5% of the total dry weight of the composition and comprises a ratio of calcium to collagen of from 0.005:1 to 10:1 by weight; and administering an effective amount of the composition by direct injection to a knee joint of a subject that has or is at risk for developing arthritis at the joint, wherein surgery has not been performed on the joint, and wherein surgery is not concurrently being performed on the joint.

2. The method of claim 1, wherein the collagen material has a pH of 7.4 to 7.5.

3. A method for treating arthritis, comprising: forming a composition by mixing together a collagen material, a calcium solution having a calcium concentration of about 30 mM to about 90 mM, and a red blood cell, wherein the collagen material is a dry powder, wherein the mixing comprises adding 1-5 mg $CaCl_2$) per 40 mg of the collagen to the composition, and wherein the composition comprises GAG in an amount of less than 10% of the total dry weight of the composition; and administering an effective amount of the composition by direct injection to a knee joint of a subject that has or is at risk for developing arthritis at the joint, wherein surgery has not been performed on the joint, and wherein surgery is not concurrently being performed on the joint.

4. The method of claim 3, wherein the arthritis is osteoarthritis.

5. The method of claim 3, wherein the subject has a partial cartilage injury.

6. The method of claim 3, wherein the subject has early osteoarthritis.

7. The method of claim 3, wherein the collagen material is a lyophilized collagen material.

8. The method of claim 3, wherein the composition is a slurry.

9. The method of claim 3, wherein the composition is a gel.

10. The method of claim 3, wherein the collagen material comprises:
   a phospholipid in an amount less than 125 μM/mg;
   a nucleic acid in an amount less than 100 μg/g; and
   an active pepsin in an amount less than 10,000 μg/ml.

11. The method of claim 3, wherein the composition comprises GAG in an amount of less than 5% of the total dry weight of the composition.

12. The method of claim 3, wherein the composition consists essentially of the collagen material, the red blood cell, the calcium solution, the GAG, and water.

13. A method for treating arthritis, comprising: forming a liquid composition by mixing together a collagen material, a calcium solution having a calcium concentration of about 30 mM to about 90 mM, and a red blood cell, the composition comprising GAG in an amount of less than 10% of the total dry weight of the composition, the composition comprising a ratio of calcium to collagen of from 0.005:1 to 10:1 by weight, wherein the collagen material is a dry powder, and wherein the collagen material comprises:
   a phospholipid in an amount less than 125 μM/mg;
   a nucleic acid in an amount less than 100 μg/g; and
   an active pepsin in an amount less than 10,000 μg/ml; and
   administering an effective amount of the composition by direct injection to a knee joint of a subject that has or is at risk for developing arthritis at the joint, wherein surgery has not been performed on the joint, and wherein surgery is not concurrently being performed on the joint.

* * * * *

UNITED STATES PATENT AND TRADEMARK OFFICE
CERTIFICATE OF CORRECTION

PATENT NO. : 11,484,578 B2
APPLICATION NO. : 14/376212
DATED : November 1, 2022
INVENTOR(S) : Martha M. Murray and Braden C. Fleming It is certified that error appears in the above-identified patent and that said Letters Patent is hereby corrected as shown below:

On the Title Page

Column 1, item (87) (PCT Pub. No.), Line 1, delete "WO 2004/078134" and insert -- WO 2013/116744 --;

Column 1, item (87), (PCT Pub. Date), Line 1, delete "Sep. 16, 2004" and insert -- Aug. 8, 2013 --.

In the Claims

Column 40, Line 52, Claim 3, delete "CaCl2)" and insert -- $CaCl_2$ --.

Signed and Sealed this
First Day of April, 2025

Coke Morgan Stewart
*Acting Director of the United States Patent and Trademark Office*